(12) United States Patent
Thomas

(10) Patent No.: US 6,667,153 B1
(45) Date of Patent: Dec. 23, 2003

(54) COMPOSITION AND METHOD FOR DETECTING MUTAGENS

(75) Inventor: Susan Margaret Thomas, 4 Saunders St., Mitcham SA 5062 (AU)

(73) Assignee: Susan Margaret Thomas, Mitcham (AU)

( * ) Notice: Subject to any disclaimer, the term of this patent is extended or adjusted under 35 U.S.C. 154(b) by 0 days.

(21) Appl. No.: 09/603,448

(22) Filed: Jun. 26, 2000

(51) Int. Cl.[7] ................. C12Q 1/68; C12Q 19/34; C07H 21/02
(52) U.S. Cl. ............ 435/6; 435/91.2; 536/23.1; 536/24.3; 536/24.31; 536/24.33
(58) Field of Search .................. 435/6, 91.2; 536/23.1, 536/24.3, 24.31, 24.33

(56) References Cited

U.S. PATENT DOCUMENTS

| | | |
|---|---|---|
| 5,491,084 A | 2/1996 | Chalfie et al. |
| 5,589,337 A | 12/1996 | Farr |
| 5,625,048 A | 4/1997 | Tsien et al. |
| 5,702,883 A | 12/1997 | Imaeda et al. |
| 5,776,681 A | 7/1998 | Virta et al. |
| 5,777,079 A | 7/1998 | Tsien et al. |
| 5,804,387 A | 9/1998 | Cormack et al. |
| 5,958,713 A | 9/1999 | Thastrup et al. |
| 5,994,077 A | 11/1999 | Valdivia et al. |
| 5,998,159 A | 12/1999 | Watson et al. |
| 5,998,204 A | 12/1999 | Tsien et al. |
| 6,004,764 A | 12/1999 | Bishai et al. |
| 6,027,881 A | 2/2000 | Pavlakis et al. |
| 6,046,014 A | 4/2000 | Lagarias et al. |
| 6,046,925 A | 4/2000 | Tsien et al. |
| 6,054,321 A | 4/2000 | Tsien et al. |

FOREIGN PATENT DOCUMENTS

| | | |
|---|---|---|
| WO | WO 96/23810 | 8/1996 |

OTHER PUBLICATIONS

Mitchell et al, "Investigations into parametric analysis of data from in vivo micronucleus assays by comparison with non–parametric methods", Mutation Research 159:139–146, Jan. 1986.*

Ames, B. et al., "Methods for detecting carcinogens and mutagens with the salmonella/mammalian–microsome mutagenicity test", *Mutation Research*, vol. 31, No. 6, pp. 347–364 (Dec. 1975).

Baldwin, T. et al., "Cloning and Expression of the luxY Gene from *Vibrio fischeri* Strain Y–1 in *Escherichia coli* and Complete Amino Acid Sequence of the Yellow Fluorescent Protein", *Biochemistry*, vol. 29, No. 23, pp. 5509–5515 (Jun. 12, 1990).

Chalfie, M. et al., "Green Fluorescent Protein as a Marker for Gene Expression", *Science*, vol. 263, pp. 802–805 (Feb. 11, 1994).

Ching–Y. et al., "Multiple Promoters for Transcription of the *Escherichia coli* DNA Topoisomerase I Gene and Their Regulation by DNA Supercoiling", *J. Mol. Biol.*, vol. 202, pp. 735–742 (1988).

Cormack, B. et al., "FACS–optimized mutants of the green fluorescent protein (GFP)", *Gene*, vol. 173, No. 1, pp. 33–38 (1996).

Crameri, A. et al., "Improved Green Fluorescent Protein by Molecular Evolution Using DNA Shuffling", *Nature Biotechnology*, vol. 14, No. 3, pp. 315–319 (Mar. 14, 1996).

Demple, B. et al., "Exonuclease III and endonuclease IV remove 3' blocks from DNA synthesis primers in H2O2–damaged *Escherichia coli*", *Proc. Natl. Acad. Sci. USA*, vol. 83, No. 20, pp. 7731–7735 (Oct. 1986).

Drlica, K. et al., "Inhibitors of DNA Topoisomerases", *Biochemistry*, vol. 27, No. 7, pp. 2253–2259 (Apr. 5, 1988).

Elledge, S. et al., "The muc Genes of pKM101 Are Induced by DNA Damage", *J. Bacteriol.*, vol. 155, No. 3, pp. 1306–1315 (Sep. 1983).

Ellenberg, J. et al., "Dual–colour imaging with GFP variants", *trends in Cell Biology*, vol. 9, pp. 52–56 (Feb. 1999).

Farr, S. et al., "Oxidative Stress Responses in *Escherichia coli* and *Salmonella typhimurium*", *Microbiol. Rev.*, vol. 55, No. 4, pp. 561–585 (Dec. 1991).

Heim, R. et al., "Wavelength mutations and posttranslational autoxidation of green fluorescent protein", *Proc. Natl. Acad. Sci. USA*, vol. 91, No. 26, pp. 12501–12504 (Dec. 20, 1994).

Heim, R. et al., "Improved Green fluorescence", *Nature*, vol. 373, No. 6514, pp. 663–664 (Feb. 23, 1995).

Heim, R. et al., "Engineering green fluorescent protein for improved brightness, longer wavelengths and fluorescence resonance energy transfer", *Current Biology*, vol. 6, No. 2, pp. 178–182 (Feb. 1, 1996).

Herrero, M. et al., "Transposon Vectors Containing Non–Antibiotic Resistance Selection Markers for Cloning and Stable Chromosoal Insertion of Foreign Genes in Gram–Negative Bacteria", *J. Bacteriol.*, vol. 172, No. 11, pp. 6557–6567 (Nov. 1990).

Inouye, S. et al., "Evidence for redox forms of the Aequorea green fluorescent protein", *FEBS Letters*, vol. 351, No. 2, pp. 211–214 (Sep. 5, 1994).

(List continued on next page.)

Primary Examiner—Jeffrey Fredman
(74) Attorney, Agent, or Firm—Merchant & Gould P.C.

(57) ABSTRACT

The present invention relates to methods and compositions for detecting a mutagen. The compositions include a DNA construct, an expression vector, and a host cell including a mutagen sensitive gene operably linked to a fluorescent protein. The method includes exposing a host cell including a mutagen sensitive gene operably linked to a fluorescent protein and monitoring expression of the fluorescent protein.

19 Claims, 16 Drawing Sheets

OTHER PUBLICATIONS

Ito, Y. et al., "A Novel Mutant of Green Fluorescent Protein with Enhanced Sensitivity for Microanalysis at 488 nm Excitation", *Biochemical and Biophysical Research Communications*, vol. 264, No. 2, pp. 556–560, (Oct. 22, 1999).

Justus, T. et al., "Construction of a umuC'–luxAB plasmid for the detection of mutagenic DNA repair via luminescence", *Mutation Research*, vol. 398, pp. 131–141 (1998).

Justus, T. et al., "Evaluation of transcriptional fusions with green fluorescent protein versus luciferase as reporters in bacterial mutagenicity tests", *Mutagenesis*, vol. 14, No. 4, pp. 351–356 (1999).

Kitagawa, Y. et al., Structural analysis of the umu operon required for inducible mutagenesis in *Escherichia coli*, *Proc. Natl. Acad. Sci. USA*, vol. 82, pp. 4336–4340 (Jul. 1985).

Langer, P. et al., "Functional Organization of Plasmid pKM101", *J. Bacteriol.*, vol. 143, No. 3, pp. 1310–1316 (Mar. 1981).

Levine, L. et al., "Isolation and characterization of a photoprotein, "phialidin", and a spectrally unique green–fluorescent protein from the bioluminescent jellyfish *phialidium gregarium*", *Comp. Biochem. Physiol.*, vol. 72B, No. 1, pp. 77–85 (1982).

Li, L. et al., "Continuous Fluorescence Assay of Phytochrome Assembly in Vitro", *Biochemistry*, vol. 34, No. 24, pp. 7923–7930 (Jun. 26, 1995).

Lilley, D.M.J. et al., "Local DNA topology and gene expression: the case theu–500 promoter", *Molecular Microbiology*, vol. 5, No. 4, pp. 779–783 (Apr. 1991).

Maki, H. et al., "MutT protein specifically hydrolyses a potent mutagenic substrate for DNA synthesis", *Nature*, vol. 355, No. 6357, pp. 273–275 (Jan. 16, 1992).

Marsh, L. et al., "Cold Sensitivity Induced by Overproduction of UmuDC in *Escherichia coli*", *J. Bacteriol.*, vol. 162, No. 1, pp. 155–161 (Apr. 1985).

Matthysse, A. et al., Construction of GFP vectors for use in Gram–negative bacteria other than *Escherichia coli*, *FEMS Microbiology Letters*, vol. 145, No. 1, pp. 87–94 (Nov. 15, 1996).

Nakabeppu, Y. et al., "Purification and Structure of the Intact Ada Regulatory Protein of *Escherichia coli* K12, $O^6$–Methylguanine–DNA Methyltransferase", *J. Biol. Chem*, vol. 260, No. 12, pp. 7281–7288 (Jun. 25, 1985).

Norris, B. et al., "Nucleotide sequence of a cDNA clone encoding the precursor of the peridinin–chlorophyll a–binding protein from the dinoflagellate Symbiodinium sp.", *Plant Molecular Biology*, vol. 24, No. 4, pp. 673–677 (Feb. 1994).

Perry, K. et al., "Identification of plasmid (pKM101)–coded proteins involved in mutagenesis and UV resistance", *Nature*, vol. 300, No. 5889, pp. 278–281 (Nov. 18, 1982).

Perry, K. et al., "umuDC and mucAB operons whose products are required by UV light– and chemical–induced mutagenesis: UmuD, MucA, and LexA proteins share homology", *Proc. Natl. Acad. Sci. USA*, vol. 82, No. 13, pp. 4331–4335 (Jul. 1985).

Prasher, D. et al., "Primary structure of the *Aequorea victoria* green–fluorescent protein", *Gene*, vol. 111, No. 2, pp. 229–233 (1992).

Shinagawa, H. et al., "Cloning and characterization of the umu operon responsible for inducible mutagenesis in *Escherichia coli*", *Gene*, vol. 23, No. 2, pp. 167–174 (Aug. 1983).

Smith, C. et al., "Sequence Analysis andMapping of the *Salmonella typhimurium* LT2 umuDC Operon", *J. Bacteriol.*, vol. 172, No. 9, pp. 4964–4978 (Sep. 1990).

Tanooka, H. et al., "Heterospecific Expression of Misrepair–Enhancing Activity of mucAB in *Escherichia coli* and *Bacillus subtilis*", *J. Bacteriol.*, vol. 173, No. 9, pp. 2906–2914 (May 1991).

Thomas, S. et al., "Structural Characterization of the *Salmonella typhimurium* LT2 umu Operon", *J. Bacteriol.*, vol. 172, No. 9, pp. 4979–4987 (Sep. 1990).

Tsien, R. et al., "FRET for studying intracellular signalling", *trends in Cell Biology*, vol. 3, pp. 242–245 (Jul. 1993).

Ward, W. et al., "Spectral pertubations of the Aequorea green–fluorescent protein", *Photochem. Photobiol.*, vol. 35, No. 6, pp. 803–808 (Jun. 1982).

Wilbanks, S. et al., "Rod Structure of a Phycoerythrin II–containing Phycobilisome", *J. Biol. Chem.*, vol. 268, No. 2, pp. 1226–1235 (Jan. 15, 1993).

"AutoFluorescent Proteins and Fusion Vectors. AutoFluorescent Proteins AFP®: Vital fluorescent tags and reporter systems", *Quantum Biotechnologies*, 5 pages (Date Unknown).

"Autofluorescent Proteins & Fusion Vectors. Characteristics of the AFPS™ From GFP to AFPs™", *Quantum Biotechnologies*, http://www.qbi.com/Products/autofluorescent2c.html, 4 pages (Printed Jun. 14, 2000).

"Living Colors™ Fluorescent Proteins",*Clontech Now You Can*, 8 pages ©1997, 1998 Clontech Laboratories, Inc.).

"Living Colors® Product List", *Clontech Laboratories, Inc.*, pp. 1–6 (Apr. 1999).

"Living Colors® Red Fluorescent Protein. The only red fluorescent protein for expression studies", *Clontechniques*, pp. 1–5 (Oct. 1999).

"PQBI 25", *Quantum Biotechnologies*, 19 pages (Date Unknown).

* cited by examiner

Figure 7 Histogram of mutant colony numbers from 40 parallel cultures following exposure to MNNG
0 μg/ml ■
0.1μg/ml ■
3.5μg/ml ▢
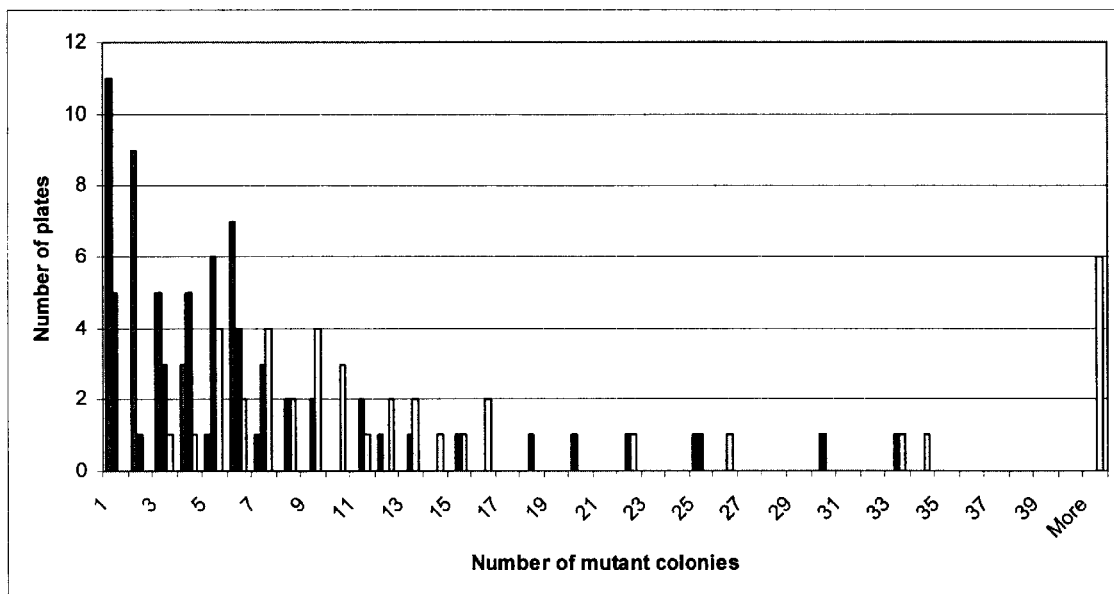

Figure 8    Histogram of mutant colony numbers from 37 parallel cultures following exposure to MMS
0 µg/ml
13 µg/ml
325 µg/ml
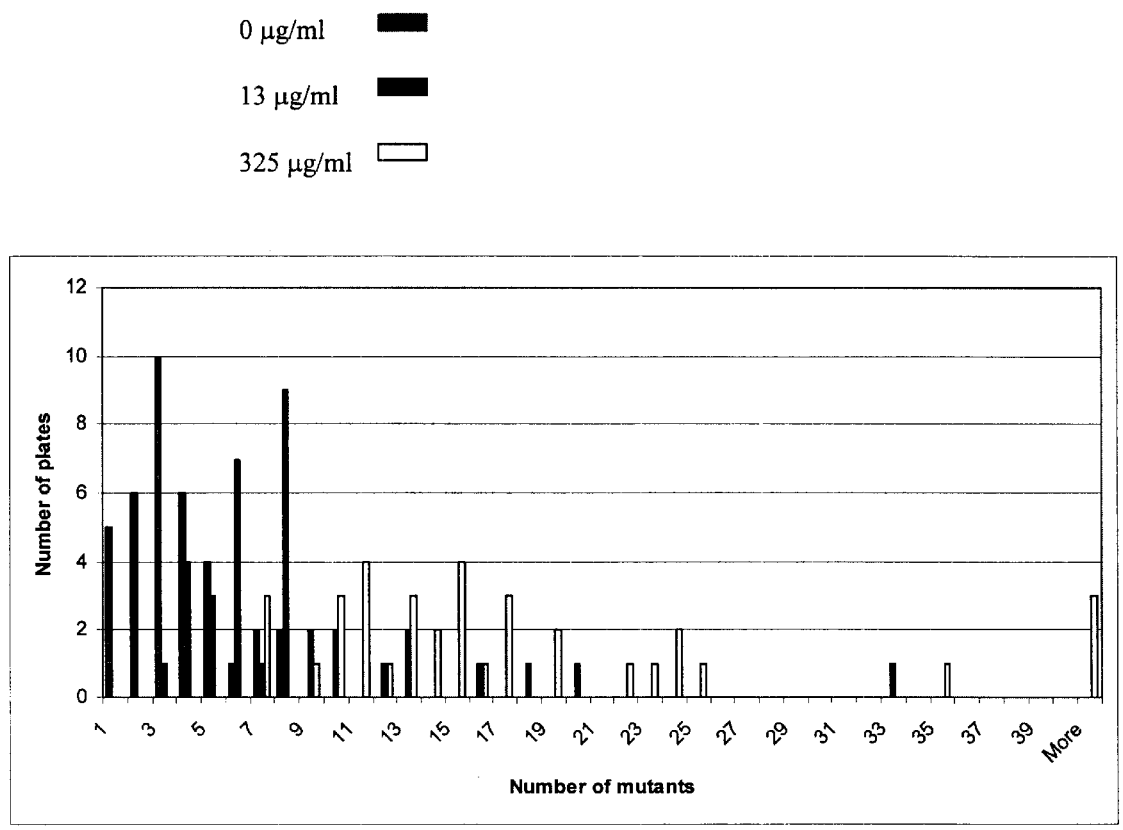

Figure 9   Histograms of mutant colony numbers and fluorescence emission from 24 parallel cultures following exposure to MNNG
0 μg/ml    ■    1.7 μg/ml    ■
a.) Fluorescence emission values
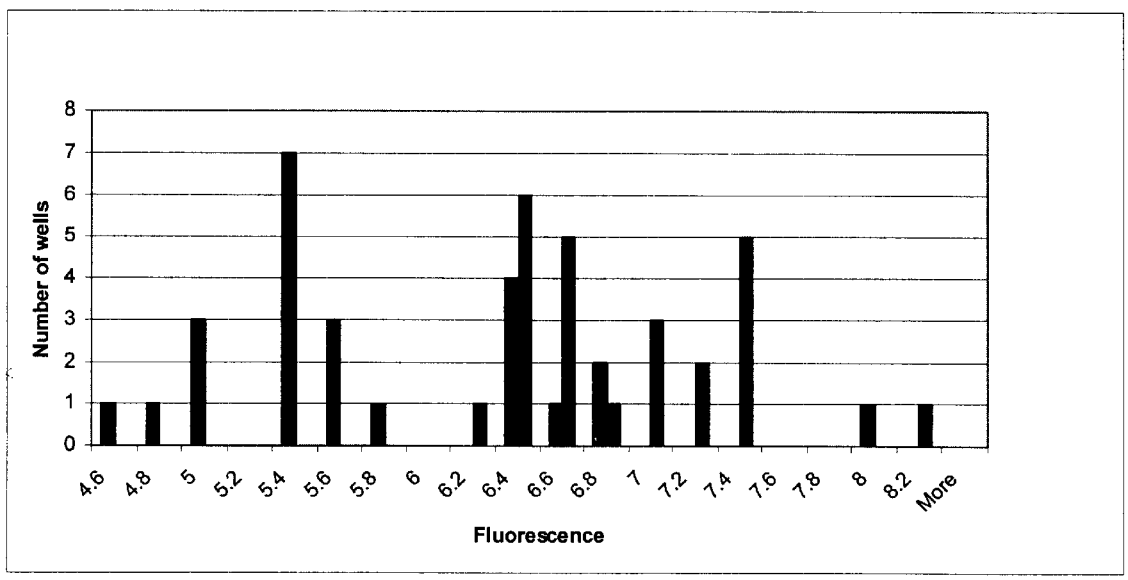
b.) Revertant colony numbers
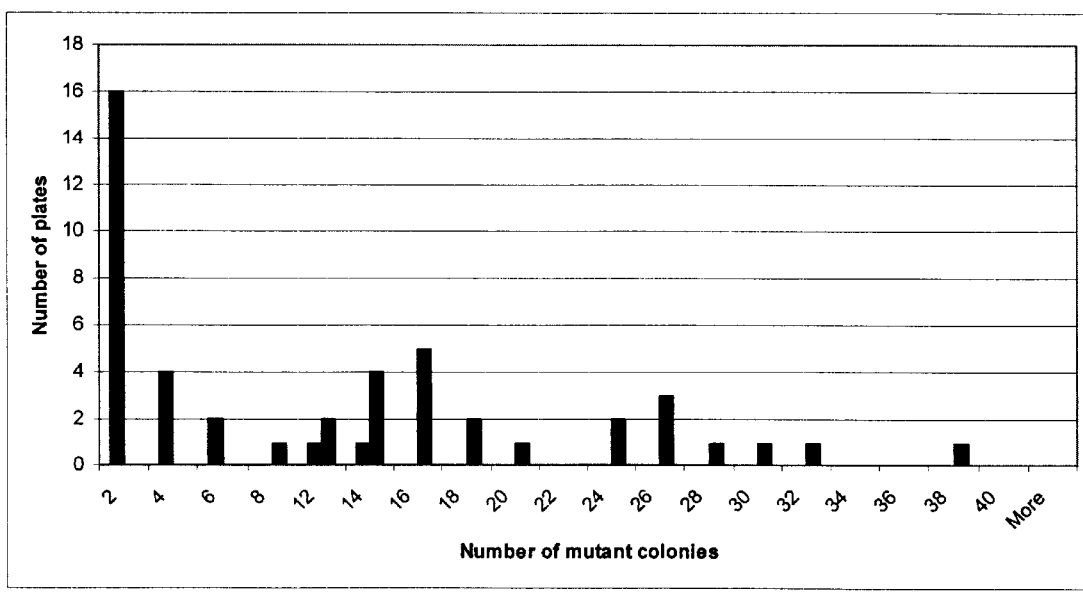

Figure 10    Histogram of fluorescence emission from 84 parallel cultures following exposure to MMS
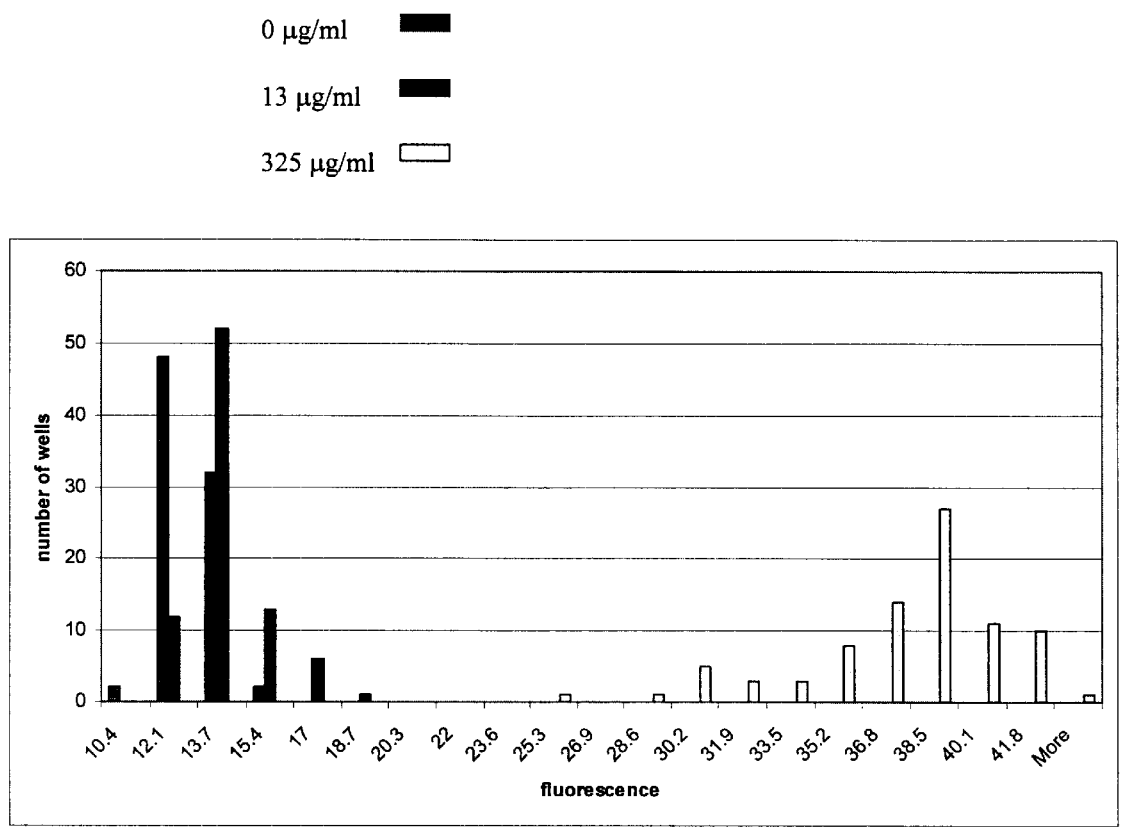

Figure 11   Histogram of fluorescence emission from 84 parallel cultures following exposure to MNNG
0 μg/ml ▬
0.1 μg/ml ▬
3.5 μg/ml ▭
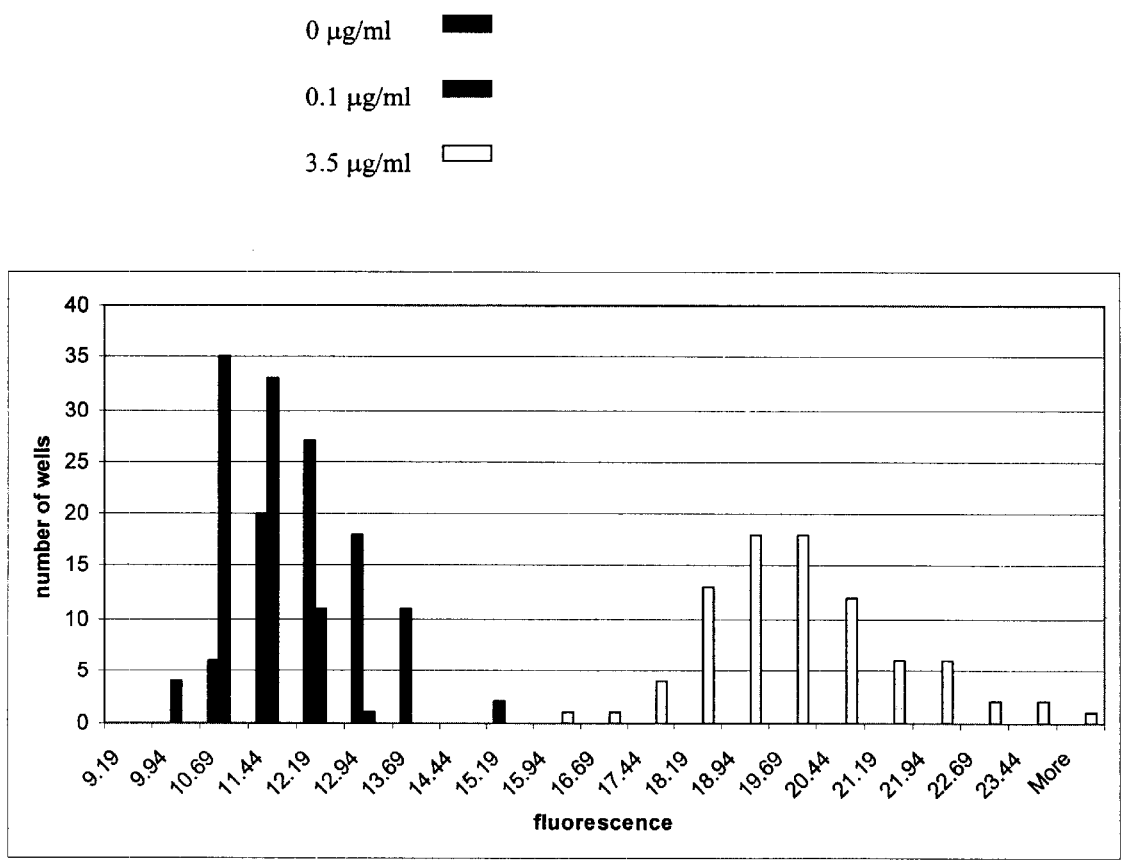

Figure 12  Histogram of fluorescence emission from 84 parallel cultures following exposure to 254nm UVC
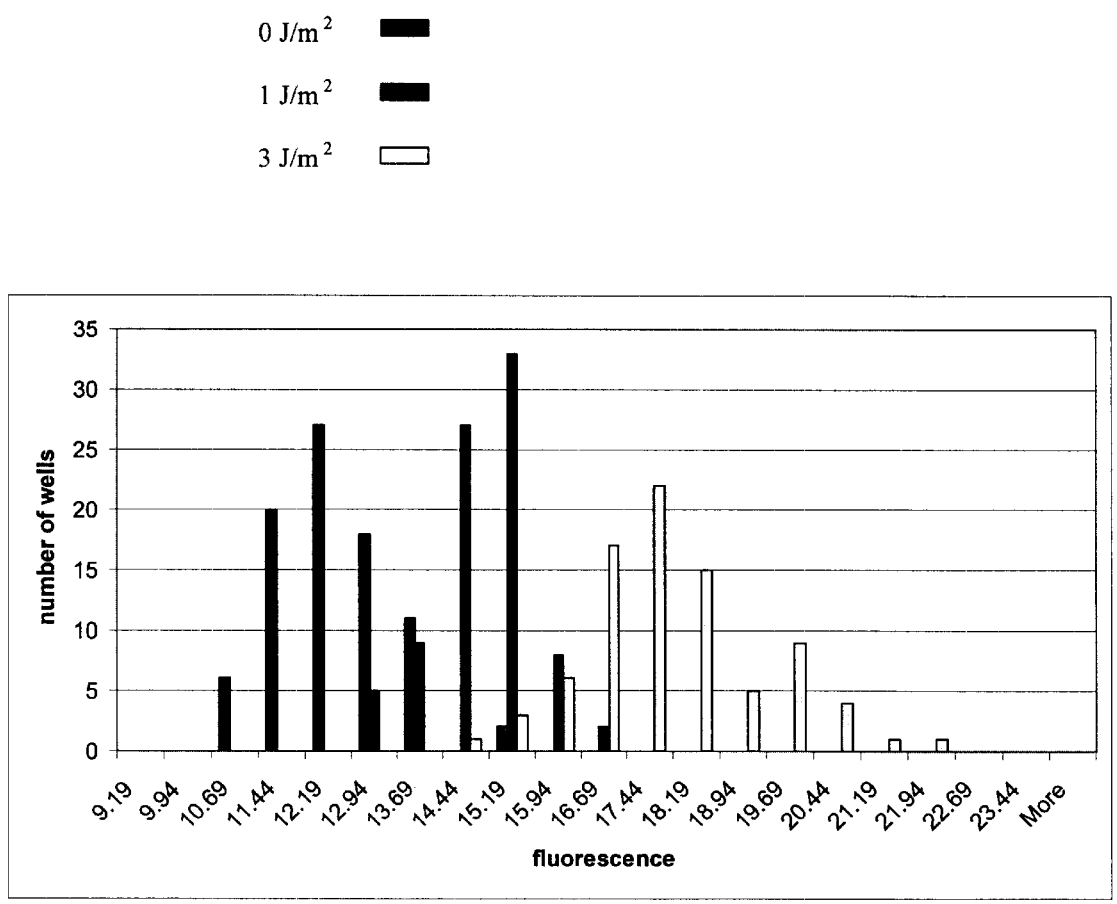

Figure 13

GenBank ACCESSION M13387 umuD protein

MLFIKPADLREIVTFPLFSDLVQCGFPSPAADYVEQRIDLNQLL

IQHPSATYFVKASGDSMIDGGISDGDLLIVDSAITASHGDIVIAAVDGEFTVKKLQLR
PTVQLIPMNSAYSPITISSEDTLDVFGVVIHVVKAMR"

umuC protein

MFALCDVNAFYASCETVFRPDLWGKPVVVLSNNDGCVIARNAEA

KALGVKMGDPWFKQKDLFRRCGVVCFSSNYELYADMSNRVMSTLEELSPRVEIYSIDE

AFCDLTGVRNCRDLTDFGREIRATVLQRTHLTVGVGIAQTKTLAKLANHAAKKWQRQT

GGVVDLSNLERQRKLMSALPVDDVWGIGRRISKKLDAMGIKTVLDLADTDIRFIRKHF

NVVLERTVRELRGEPCLQLEEFAPTKQEIICSRSFGERITDYPSMRQAICSYAARAAE

KLRSEHQYCRFISTFIKTSPFALNEPYYGNSASVKLLTPTQDSRDIINAATRSLDAIW

QAGHRYQKAGVMLGDFFSQGVAQLNLFDDNAPRPGSEQLMTVMDTLNAKEGRGTLYFA
GQGIQQQWQMKRAMLSPRYTTRSSDLLRVK

The Gene

```
  1 aaaatcagca gcctatgcag cgacaaatat tgatagcctg aatcagtatt gatctgctgg
 61 caagaacaga ctactgtata taaaaacagt ataacttcag gcagattatt atgttgttta
121 tcaagcctgc ggatctccgc gaaattgtga cttttccgct atttagcgat cttgttcagt
181 gtggcttttcc ttcaccggca gcagattacg ttgaacagcg catcgatctg aatcaactgt
241 tgatccagca tcccagcgcg acttacttcg tcaaagcaag tggtgattct atgattgatg
301 gtggaattag tgacggtgat ttactgattg tcgatagcgc tattaccgcc agccatggtg
361 atattgtcat cgctgctgtt gacggcgagt ttacggtgaa aaaattgcaa ctacgcccga
421 cggtacagct tattcccatg aacagcgcgt actcgcccat taccatcagt agtgaagata
481 cgctggatgt ctttggtgtg gtgatccacg tcgttaaggc gatgcgctga tgtttgccct
541 ctgtgatgta aacgcgtttt atgccagctg tgagacggtg tttcgccctg atttatgggg
601 taaaccggtg gttgtgctat cgaataatga cggttgcgtt atcgcccgaa acgctgaggc
```

```
 661 aaaggcgctt ggcgttaaaa tgggcgatcc ctggttcaaa caaaaagatc tgtttcgtcg
 721 ctgtggcgtg gtttgcttta gcagcaatta tgagctttac gcagacatga gcaatcgggt
 781 gatgtcgacg ctggaagagc tatcgccccg cgtcgagatt tacagtattg atgaggcatt
 841 ctgcgatctg acaggtgtgc gtaattgtcg cgatctgact gattttggca gagaaattcg
 901 cgcaacggtg ctacaacgta cccatcttac tgttggtgtg gggatcgccc agaccaaaac
 961 gctggctaag cttgccaatc atgcggcaaa aaaatggcag cggcagacgg gtggggtggt
1021 ggatttatca aatctggaac gccagcgtaa attaatgtct gctctccccg tggatgacgt
1081 ctgggggatt ggacggcgga tcagcaaaaa actggacgcg atggggatca aaaccgttct
1141 cgatttggcg gatacagata tccggtttat ccgtaaacat tttaatgtcg tgctcgaaag
1201 aacggtgcgt gaactgcgcg gcgaaccctg tttgcaactg gaagagtttg caccgacgaa
1261 gcaggaaatt atctgttccc gctcgtttgg tgaacgcatc acggattatc cgtcgatgcg
1321 gcaggccatt tgtagttacg ctgcccgggc ggcggaaaaa cttcgcagcg agcatcaata
1381 ttgtcggttt atctccacgt ttattaagac gtcaccattt gcgctcaatg aaccttatta
1441 cggcaatagc gcgtcggtaa aactgctgac gcccactcag gacagcaggg atatcattaa
1501 cgctgctacg cgatctctgg atgccatctg gcaagcgggc catcgttacc aaaaagcggg
1561 cgtgatgctg ggggatttct tcagtcaggg agtcgcgcag ctcaatttat tcgatgacaa
1621 cgcaccgcgc cccgggagtg agcaattgat gacggtaatg gatacactga atgctaaaga
1681 gggcagagga acactctatt ttgccgggca ggggatccag caacaatggc agatgaagcg
1741 agccatgctt tcaccacgtt atacaacgcg aagttctgat ttactgaggg tcaaataaat
1801 atagcggcag gaaaaaa
```

Fig 13, cont'd

Figure 14 gfp mut2 protein
MSKGEELFTGVVPILVELDGDVNGHKFSVSGEGEGDATYGKLTLKFICTTGKLPVPW
PTLVTTFAYGLQCFARYPDHMKQHDFFKSAMPEGYVQERTIFFKDDGNYKTRAEVK
FEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAA
GITHGMDELYK gene
  1 aagctttatt aaaatgtcta aaggtgaaga attattcact ggtgttgtcc aattttggt
 61 tgaattagat ggtgatgtta atggtcacaa attttctgtc tccggtgaag gtgaaggtga
121 tgctacttac ggtaaattga ccttaaaatt tatttgtact actggtaaat tgccagttcc
181 atggccaacc ttagtcacta ctttcgcgta tggtcttcaa tgttttgcta gatacccaga
241 tcatatgaaa caacatgact ttttcaagtc tgccatgcca gaaggttatg ttcaagaaag
301 aactattttt ttcaaagatg acggtaacta caagaccaga gctgaagtca agtttgaagg
361 tgataccttagttaatagaa tcgaattaaa aggtattgat tttaaagaag atggtaacat
421 tttaggtcac aaattggaat acaactataa ctctcacaat gtttacatca tggctgacaa
481 acaaaagaat ggtatcaaag ttaacttcaa aattagacac aacattgaag atggttctgt
541 tcaattagct gaccattatc aacaaaatac tccaattggt gatggtccag tcttgttacc
601 agacaaccat tacttatcca ctcaatctgc cttatccaaa gatccaaacg aaaagagaga
661 ccacatggtc ttgttagaat tgttactgc tgctggtatt acccatggta tggatgaatt
721 gtacaaataa ctgcag

Figure 15

The structure and sequence of the construct

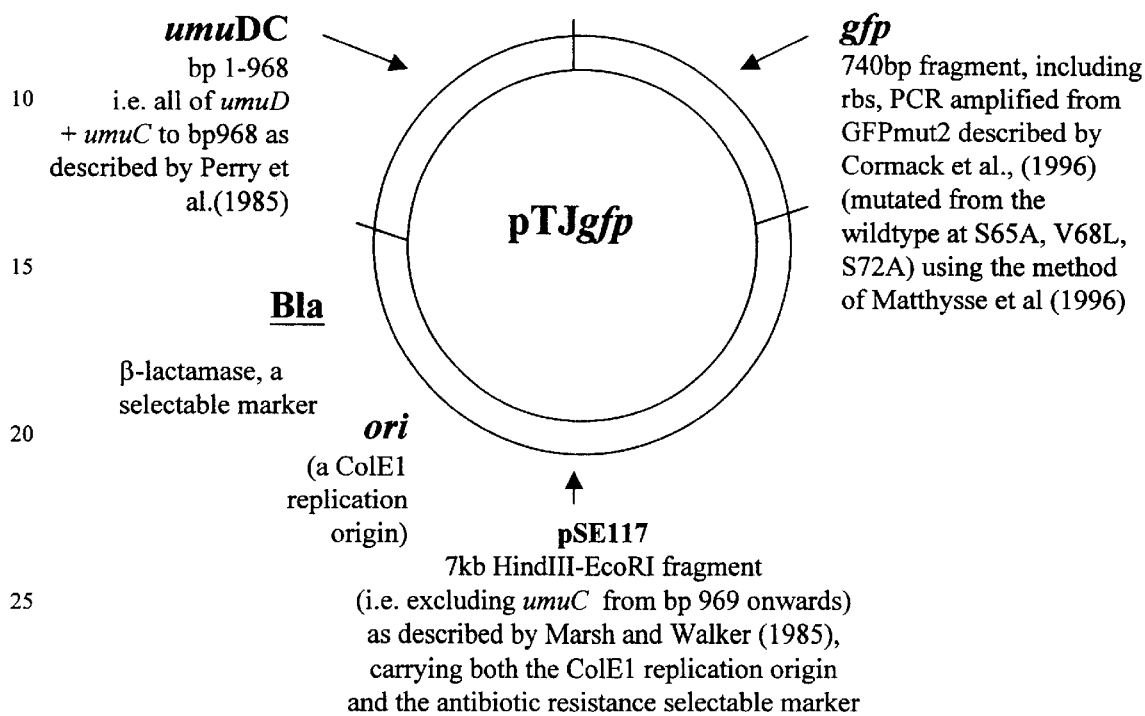

umuDC
bp 1-968
i.e. all of *umuD*
+ *umuC* to bp968 as
described by Perry et
al.(1985)

Bla
β-lactamase, a
selectable marker ori
(a ColE1
replication
origin)

gfp
740bp fragment, including
rbs, PCR amplified from
GFPmut2 described by
Cormack et al., (1996)
(mutated from the
wildtype at S65A, V68L,
S72A) using the method
of Matthysse et al (1996)

pSE117
7kb HindIII-EcoRI fragment
(i.e. excluding *umuC* from bp 969 onwards)
as described by Marsh and Walker (1985),
carrying both the ColE1 replication origin
and the antibiotic resistance selectable marker

COMPOSITION AND METHOD FOR DETECTING MUTAGENS

FIELD OF THE INVENTION

The present invention relates to methods and compositions for detecting a mutagen. The compositions include a DNA construct, an expression vector, and a host cell including a mutagen sensitive gene operably linked to a fluorescent protein. The method includes exposing a host cell including a mutagen sensitive gene operably linked to a fluorescent protein and monitoring the fluorescent protein.

BACKGROUND OF THE INVENTION

The current increased awareness of environmental contamination by diverse classes of chemicals has led to increasing concern about the impact of this contamination on human health. Some of these environmental contaminants may be toxic and/or carcinogenic, which emphasizes the need for rapid and inexpensive screening methods for the hazards of environmental contaminants. Many existing tests for carcinogens are based on animal models or tissue culture techniques, which are both time-consuming and costly. These animal and tissue culture tests can be supplemented with simpler tests on bacterial cell cultures. However, the most widespread bacterial mutagenicity the test, the Ames test, requires repeated culturing of many cell samples, lengthy incubation, and tedious analysis. These consume time, money, and reagents. There exists a need for simpler and more robust bacterial or cell culture tests for mutagens.

SUMMARY OF THE INVENTION

The present invention relates to methods and compositions for detecting a mutagen. The compositions include a DNA construct, an expression vector, and a host cell each including a mutagen sensitive gene operably linked to a fluorescent protein. The method includes exposing a host cell including a mutagen sensitive gene operably linked to a fluorescent protein and monitoring the fluorescent protein. The present invention includes a DNA construct including a mutagen sensitive gene operably linked to the coding sequence for a fluorescent protein. In a preferred embodiment, the mutagen sensitive gene includes an SOS gene. The SOS gene can include one or more promoters or coding sequences whose expression is induced or up regulated in a cellular response to a mutagen. A preferred SOS gene is derived from E. coli or S. typhimurium and includes a umuC gene, a umuD gene, a control sequence for either of these genes, or a combination thereof. The DNA construct of the invention can include the coding sequence for any of a variety of fluorescent proteins. Preferably, the fluorescent protein is a green fluorescent protein, preferably from the jellyfish Aequorea victoria. The coding sequence for the fluorescent protein can encode a variant green fluorescent protein. The mutagen sensitive gene and/or the fluorescent protein gene can be a naturally occurring or variant gene or protein. The expression construct can encode a protein of the invention, a polypeptide including an amino acid sequence of a UmuD protein, a UmuC protein, or a combination thereof and an amino acid sequence of a fluorescent protein.

The invention also includes an expression vector including a mutagen sensitive gene operably linked to a coding sequence for a fluorescent protein. The expression vector can include the DNA construct of the invention. Preferably, the expression vector includes an SOS gene, or variant thereof, derived from plasmid pSE 117 and a coding sequence for a fluorescent protein. A preferred plasmid expression vector is pTJgfp.

In another embodiment, the invention includes a host cell including a mutagen sensitive gene operably linked to a coding sequence for a fluorescent protein. Preferred host cells include S. typhimurium and E. coli. The host cell can include a DNA construct or expression vector of the invention. Alternatively, the host cell can have its genomic DNA altered to include a heterologous mutagen sensitive gene operably linked to a homologous coding sequence for a fluorescent protein or to include a heterologous coding sequence for a fluorescent protein operably linked to a homologous mutation sensitive gene.

In one embodiment, the invention includes a method of determining or detecting a mutagen. The method includes contacting a test compound with a host cell of the invention, monitoring the host cell for the fluorescent protein, and, when an amount or distribution of the fluorescent protein meets or exceeds a predetermined threshold value, determining that the test compound is a mutagen. The method can employ a host cell either at stationary phase or at logarithmic phase. Contact with the test compound can deplete a nutrient, or even starve the host cell, and the method will still robustly detect a mutagen. Preferably, when contacting depletes a nutrient or starves a cell, the cells are in a logarithmic phase. Monitoring fluorescent protein typically includes detecting fluorescence, such as with a fluorescence detector that reads a microtiter plate. The mutagen can be detected through increases in the level or output of fluorescence compared to a control sample. Alternatively, the mutagen can be determined or detected by statistically analyzing the amount of green fluorescent protein in replicate wells. The statistical analysis can include analysis of the location, shape, or distribution of fluorescent output, cells, or other data.

BRIEF DESCRIPTION OF THE FIGURES

FIG. 7 illustrates a histogram representing mutant colony numbers from 40 parallel cultures following exposure to MNNG: ☐0 μg/ml, ■0.1 μg/ml, ☐3.5 μg/ml.

FIG. 8 illustrates a histogram representing mutant colony numbers from 37 parallel cultures following exposure to MMS: ☐0 μg/ml, ■13 μg/ml, ☐325 μg/ml.

FIGS. 9a and 9b illustrate histograms representing mutant colony numbers and fluorescence emission from 24 parallel cultures following exposure to MNNG: ☐0 μg/ml, ■1.7 μg/ml; a.) fluorescence emission values; b.) revertant colony numbers.

FIG. 10 illustrates a histogram representing fluorescence emission from 84 parallel cultures following exposure to MMS: ☐0 μg/ml, ■13 μg/ml, ☐325 μg/ml.

FIG. 11 illustrates a histogram representing fluorescence emission from 84 parallel cultures following exposure to MNNG: ■0 μg/ml, ☐0.1 μg/ml, ☐3.5 μg/ml.

FIG. 12 illustrates a histogram representing fluorescence emission from 84 parallel cultures following exposure to 254 nm UV irradiation: ☐0 $J/m^2$, ■1 $J/m^2$, ☐3 $J/m^2$.

FIG. 13 illustrates a nucleotide sequence of a preferred SOS gene of the invention.

FIG. 14 illustrates a coding sequence for and the amino acid sequence of a preferred fluorescent protein of the invention.

FIG. 15 illustrates a preferred DNA construct of the invention.

DETAILED DESCRIPTION OF THE INVENTION

Definitions

Figure 1:
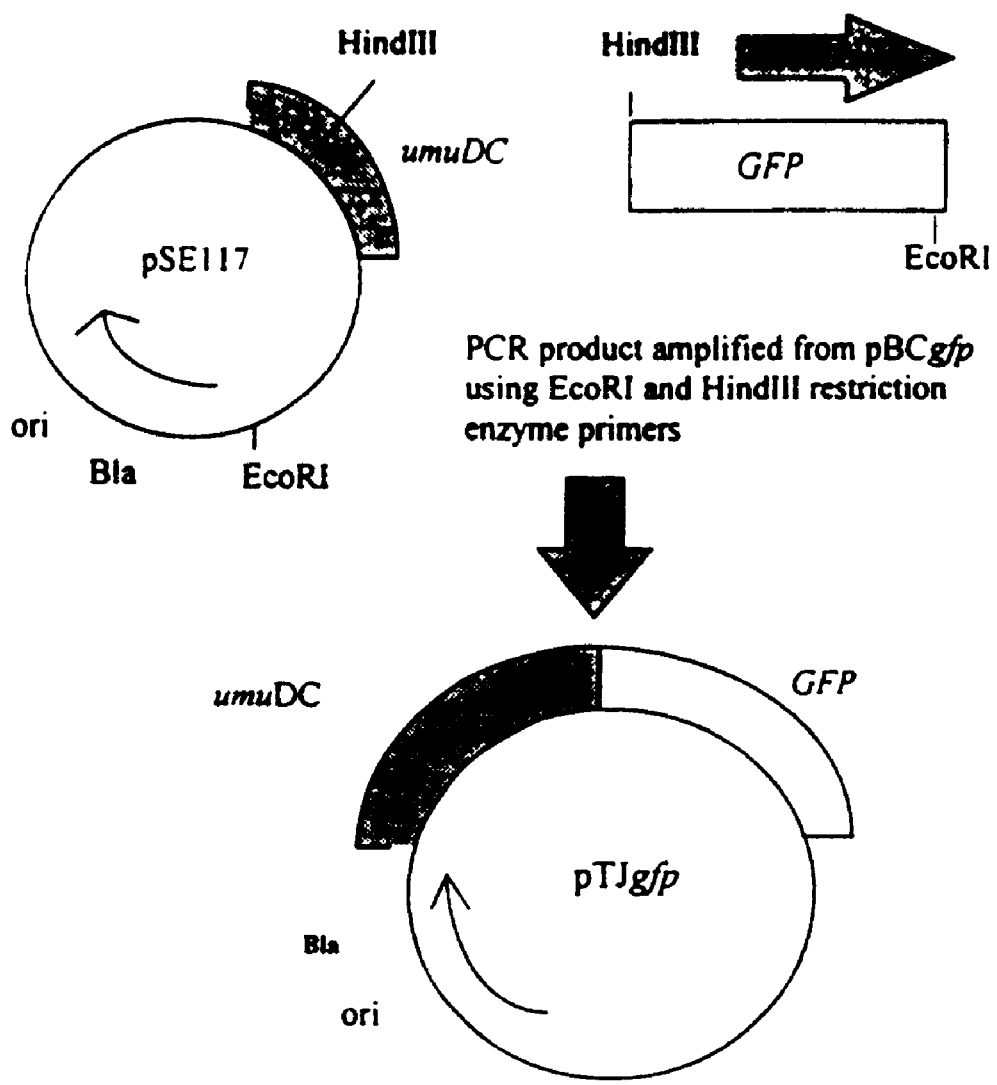
FIG. 1 illustrates construction of a umuC'::gfp fusion plasmid. A HindIII-EcoRI fragment from pSE 117 was ligated to a 700 bp gfp gene which was obtained via PCR amplification using HindIII and EcoRi primers.

As used herein, "test compound" refers to a compound to be tested for mutagenicity. The test compound can be a single compound, a mixture of compounds, even a mixture of biological materials, such as a plant extract, soil, fresh water, salt water, or the like. The test compound can also be a mixture of test compounds. The test compound can be applied to, mixed with, or contacted with a host cell of the invention in one or more of a variety of physical states. For example, the test compound may be a component of a solution that is mixed with the nutrient media for the host cell. Alternatively, the test compound may include an insoluble solid that can be suspended in or contacted with the nutrient medium. The test compound can even be a gas that is bubbled through the nutrient medium containing host cell.

As used herein, "mutagen" refers to a physical or chemical agent that is capable of increasing frequency of mutation above the spontaneous, background level. A mutagen can induce mutations in DNA and in living cells or cause biochemical damage to a gene. "Mutation" refers to the process by which genetic material undergoes a detectable and/or heritable structural change, or the result of such a change.

As used herein, "fluorescence", "fluoresce", or "fluorescent" refers to a type of luminescence in which an atom or molecule emits visible radiation in passing from a higher to a lower electronic state. These terms are restricted to phenomena in which the time interval between absorption and emission of energy is extremely short ($10^{-8}$ to $10^{-3}$ second). This distinguishes fluorescence from phosphorescence, in which the time interval may extend to several hours. Fluorescence can result from absorbing energy derived from exciting radiation of a wavelength that is usually shorter than the wavelength of the light emitted. Fluorescence can also arise from striking an atom or molecule with a subatomic particle. As used herein, fluorescence is distinct from "bioluminescence" or "chemiluminescence". Bioluminescence refers to the production of light by certain enzyme catalyzed reactions in living organisms. Chemiluminescence refers to the production of visible light occurring as a result of a chemical reaction. A fluorescent protein need not undergo an enzyme catalyzed or chemical reaction to fluoresce.

As used herein, "expression vector" means a DNA construct including a DNA sequence (e.g., a sequence encoding a fluorescent protein) which is operably linked to a suitable control sequence (e.g. all or part of a mutagen sensitive gene) capable of affecting the expression of the DNA in a suitable host. Such control sequences may include a promoter to affect transcription, an optional operator sequence to control transcription, a sequence encoding suitable ribosome-binding sites on the mRNA, and sequences which control termination of transcription and translation. Different cell types may be employed with different expression vectors. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Useful expression vectors, for example, can include segments of chromosomal, non-chromosomal and synthetic DNA sequences such as various known derivatives of known bacterial plasmids, e.g., plasmids from *E. coli* including Col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μplasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., *Molecular Cloning: A Laboratory Manual, Second Edition*, Cold Spring Harbor Press (1989).

As used herein, "signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Isolated," when used to describe the various polypeptides disclosed herein, means polypeptide that has been identified and separated and/or recovered from a component of its natural environment. Isolated polypeptide includes polypeptide in situ within recombinant cells, since at least one component of the polypeptide natural environment will not be present. Ordinarily, however, isolated polypeptide will be prepared by at least one purification step.

An "isolated" fluorescent protein nucleic acid molecule or mutagen sensitive gene nucleic acid molecule is a nucleic acid molecule that is identified and separated from at least one contaminant nucleic acid molecule with which it is ordinarily associated in the natural source of the nucleic acid. An isolated fluorescent protein nucleic acid molecule or mutagen sensitive gene nucleic acid molecule is other than in the form or setting in which it is found in nature. Isolated fluorescent protein nucleic acid molecules or mutagen sensitive gene nucleic acid molecules therefore are distinguished from the corresponding nucleic acid molecules as they exist in natural cells. However, an isolated fluorescent protein nucleic acid molecule or mutagen sensitive gene nucleic acid molecule includes fluorescent protein nucleic acid molecules or mutagen sensitive gene nucleic acid molecules contained in cells that ordinarily express fluorescent protein or mutagen sensitive gene where, for example, the nucleic acid molecule is in a chromosomal location different from that of natural cells.

As used herein, "percent (%) sequence identity" with respect to the amino acid or nucleotides sequences identified herein is defined as the percentage of amino acid residues or nucleotides in a candidate sequence that are identical with the amino acid residues or nucleotides in a fluorescent protein sequence or a mutagen sensitive gene sequence, after aligning the sequences and introducing gaps, if necessary, to achieve the maximum percent sequence identity, and not considering any conservative substitutions as part of the sequence identity.

Methods for performing sequence alignment and determining sequence identity are known to the skilled artisan, may be performed without undue experimentation, and calculations of identity values may be obtained with definiteness. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5: Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173–187 (1997); and BLASTP, BLASTN, and BLASTX algorithms (see Altschul et al. (1990) *J. Mol. Biol.* 215:403–410). Computerized programs using these algorithms are also available, and include, but are not limited to: ALIGN or Megalign (DNASTAR) software, or WU-BLAST-2 (Altschul et al., *Meth. Enzym.*, 266:460–480 (1996)); or GAP, BESTFIT, BLAST Altschul et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can determined by the Smith-Waterman homology search algorithm (*Meth. Mol. Biol.* 70:173–187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology* (Wiley Interscience Publishers, 1995).

"Stringent conditions" or "high-stringency conditions", as defined herein, may be identified by those that: (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately-stringent conditions" may be identified as described by Sambrook et al., *Molecular Cloning: A Laboratory Manual* (New York: Cold Spring Harbor Press, 1989), and include the use of washing solution and hybridization conditions (e.g., temperature, ionic strength, and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

Mutagen Sensitive Gene

As used herein, "mutagen sensitive gene" refers to any gene that responds to the presence of or action of a mutagen by altering the expression of one or more gene products. For example, a mutagen sensitive gene can increase production of a protein in response to mutagen induced DNA damage. Mutagen sensitive genes include genes having nucleic acid sequences that are either naturally occurring (wild-type) or variants of these sequences. The mutagen sensitive gene of the invention can respond to a mutagen by any of a variety of mechanisms. Preferably, the mutagen sensitive gene induces production of a protein.

A mutagen sensitive gene can be isolated from nature or can be produced by recombinant or synthetic means. The term specifically encompasses naturally-occurring isoforms or alleles of the mutagen sensitive gene, naturally-occurring variant forms, and the like. Methods for detecting, isolating, and characterizing mutagen sensitive genes are well known in the art.

SOS Gene

SOS repair or error prone repair occurs in bacteria and helps them recover from potentially lethal stresses, such as exposure to a mutagen. The SOS system mediates various cellular responses including mutagenesis, activated excision repair, and activation of latent phage genomes. Although not limiting to the present invention, mutagenesis can occur by filling gaps opposite thymine dimers by replication rather than by daughter-strand transfer. Such replication is typically inaccurate. Expression of many of the genes in the SOS regulon is controlled by the LexA protein. LexA acts as a transcriptional repressor of these unlinked genes by binding to specific sequences (LexA boxes) located within the promoter region of each LexA-regulated gene. Alignment of 20 LexA binding sites found in the *E. coli* chromosome reveals a consensus sequence of 5'-TACTG(TA)(5)CAGTA-3'. DNA sequences that exhibit a close match to the consensus sequence exhibit a low heterology index and bind LexA tightly, whereas those that are more diverged have a high heterology index and are not expected to bind LexA.

SOS-responsive genes include genes that are switched on or whose transcription is induced by the SOS repair system and control sequences for these genes. Genes switched on or induced in the SOS response or their control or coding sequences are referred to herein as "SOS genes". SOS genes of several bacteria, including *Escherichia coli* and *Salmonella typhimurium*, are known in the art and have been isolated and characterized. This is described in references including: Walker, G. C., The SOS response of *Escherichia coli*, Chapter 84 in *Escherichia coli* and *Salmonella typhimurium*: cellular and molecular biology (1987) ASM Press, Washington D.C., USA. Sanderson K. E. et al., Microbiological Reviews 59(2):241–303 (1995). Berlyn M. K. B., Linkage map of Escherichia coli K-12, edition 10: the traditional map, Microbiology & Molecular Biology Review (Washington, DC) 62(3):814–984 (1998).

SOS genes include a umu gene, such as a umuC gene, a umuD gene, or a umuDC operon, which can be found in *E. coli* and *S. typhimurium*, and a muc gene, such as a mucA gene, a mucB gene, or a mucAB operon, which can be found on transferable plasmids. SOS genes also include a col gene, such as colE1; a din gene, such as a dinA, a dinB, a dinD, a dinD1::Mud(Ap,lac), a dinF, a dinG, a dinH, a dinI or a dinY gene; an imp gene, such as an impA gene, an impB gene, an impC gene, or an impCAB operon; a lex gene, such as a lexA gene; an alk gene, such as an alkA' gene; a pri gene, such as a priA gene; a rec gene, such as a recA, a recA', a recF, a recL152, or a recN gene; a rer gene; a ruv gene, such as a ruvA or ruvB gene; a sam gene, such as a samA gene, a samB gene or a samAB operon; a sfi gene, such as a sfiA gene; a ssb gene; a sul gene, such as a sulA gene; and the like. See, e.g., Walker, G. C., Microbiol. Rev. 48(1)60–93 (1984); Langer et al., J. Bacteriol. 145, 1310–1316 (1981); Elledge et al., J. Bacteriol. 155, 1307–1315 (1983); Perry et al., Nature 300, 278–281 (1982); and H. Shinagawa et al., Gene, 23, 167 (1983).

SOS genes include mutants of these genes, homologs of these genes, and genes that complement these genes. Such mutant, homologous, and complementary genes can be isolated from bacteria, plasmids, and bacteriophages. Suitable umuC mutants include those identified by Woodgate R. et al. Journal of Bacteriology 176(16):5011–21 (1994). Suitable complementary genes can be isolated from a plasmid that complements a chromosomal gene. Such complementary genes include mucAB-like gene sequences and umu-complementing operons from plasmids R391, R446b, or R471a.

SOS genes, mutants of these genes, homologs of these genes, complements of these genes and the like can be isolated from a variety of organisms, in particular *E. coli* and *S. typhimurium*, and also Bacillus such as *B. subtilis*, Deinococcus such as *D. radiodurans*, Erwinia such as *E. chrysanthemi*, Lactococcus such as *L. lactis*, Neisseria, Paracoccus such as *P. denitrificans*, Pseudomonas such as *P. aeruginosa*, Rhodobacter such as *R. sphaeroides*, Staphylococcus such as *S. epidermidis*, Streptococcus such as *S. pneumoniae* and *S. mutans*, Streptomyces such as *S. coelicolor*, and Sulfolobus such as *S. solfataricus*.

The following sequences can provide an SOS gene for the DNA construct of the invention. The nucleotide and corresponding amino acid sequences for an *E. coli* umuDC operon encoding proteins functional in UV mutagenesis and including a promoter for this operon have been reported by Perry et al., Proc. Natl. Acad. Sci. USA 82, 4331–4335 (1985) and given GenBank accession number M13387 (SEQ ID NO: 1, SEQ ID NO: 2 and SEQ ID NO: 3) and also by Kitigawa et al. supra (GenBank accession number M10107). The nucleotide and corresponding amino acid sequences for a *S. typhimurium* plasmid R46 encoding a mucAB gene for mucA and mucB proteins have been reported by Hall et al. and given GenBank accession number X16596 (SEQ ID NO: 10, SEQ ID NO: 11, SEQ ID NO: 12 and SEQ ID NO: 13). See also, Kulaeva O. I. et al. J. Bacteriol. 177(10):2737–2743 (1995). Plasmid R46 is the parent plasmid for plasmid pKM 101. The nucleotide and corresponding amino acid sequences for the *E. coli* plasmid pKM101 encoding at least muc genes have been reported by Perry, K. L. et al. and by Tanooka et al. (Proc. Nat. Acad. Sci. USA 82(13):4331–4335 (1985) and J. Bacteriol. 173(9):2906–2914

(1991), respectively) and given GenBank accession numbers D90147 (SEQ ID NO: 14, SEQ ID NO: 15 and SEQ ID NO: 16), M13388, and M12287. The nucleotide and corresponding amino acid sequences for a *S. typhimurium* plasmid R394 encoding mucA and mucB genes have been reported by Woodgate et al. and given GenBank accession number AF039836 (SEQ ID NO: 20, SEQ ID NO: 21 and SEQ ID NO: 22). The nucleotide and corresponding amino acid sequences for a *S. typhimurium* LT2 umuDC operon have been reported by Smith et al. and Thomas et al. (J. Bacteriol. 172:4694–4978 (1990) and J. Bacteriol. 172:4979–4989 (1990), respectively) and given GenBank accession numbers M57431 and M35010 (SEQ ID NO: 17, SEQ ID NO: 18 and SEQ ID NO: 19). See also, Nohmi T. et al., J. Bacteriol. 173(3):1051–63 (1991). The disclosures of each of the GenBank accessions mentioned in this paragraph and the Perry, K. L. et al. reference are incorporated herein by reference.

The following sequences of imp genes can also provide an SOS gene for the DNA construct of the invention. The sequence of an impCAB operon has been reported by Lodwick D. et al. (Nucleic Acids Research 18(17):5045–50 (1990)). Sequences of impCAB-like genes from plasmids have been reported by Runyen-Janecky L J. et al. and Lodwick D. et al. (Infection & Immunity 67(3):1415–1423 (1999) and Molecular & General Genetics 229(1):27–30 (1991), respectively)

Preferred SOS genes include the umuC gene and the umuD gene with the corresponding control sequence, preferably of *Escherichia coli*. The nucleotide and corresponding amino acid sequences of these genes are shown in FIG. 13 (SEQ ID NO: 1, SEQ ID NO: 2 and SEQ ID NO: 3) and have been reported by Perry et al., Proc. Natl. Acad. Sci. USA 82, 4331–4335 (1985) and given GenBank accession number M13387. The umuC gene and the umuD gene are expressed under control of their natural promoter. One promoter controls the expression of both genes. This promoter is located upstream of the umuD and umuC coding sequences and, although not limiting to the present invention, is negatively regulated by the LexA protein. After DNA damage, LexA protein can be cleaved and the gene activated. The UmuD and UmuC proteins form a novel polymerase that provides the cell with the capacity to polymerize opposite DNA damage lesions.

A fragment of this sequence including nucleotides 1 to 968 of SEQ ID NO: 1 can be employed in the present constructs and methods as an SOS gene that responds to mutagens and powers expression of a fluorescent protein. A coding sequence for a heterologous protein, such as a fluorescent protein, can be expressed when inserted in place of all of part of the coding sequence of the umuC gene and/or the umuD gene, or inserted into and in reading frame with either of these coding sequences. Preferably, a heterologous coding sequence is placed into the umuC gene coding sequence at a location such as after nucleotide 968 of SEQ ID NO: 1.

Additional SOS-Like Genes

The organisms listed above include other genes for inducible DNA repair responses, such as the adaptive response, which can also be employed in the constructs and methods of the present invention. In addition, homologues and similar-function genes to the SOS genes of bacteria that have been found in the lower eukaryotes. These include the rad (e.g. rad2, rad27, rad30, rad54, and rad52), din (e.g. din7), ntg (e.g. ntg1 and ntg2), snm (e.g. snm1), rev (e.g. rev2), exonuclease-1, and small subunit of ribonucleotide reductase genes of the yeast *Saccharomyces cerevisiae*. These also include the rad and rph16+ genes of the yeast *Schizosaccharomycespombe*. See, e.g., Wolter R. et al. Molecular & General Genetics 250(2):162–8 (1996) and Mitchel R. E. et al. Mutation Research 183(2):149 (1987). The fission yeast include suitable genes in their UVDR DNA repair pathway. SOS-like genes can also be found in fungi including *Neurospora crassa, Ustilago maydis*, Aspergillus sp (e.g. *spergillus nidulans*), and protists. See, Lee M. G. et al. Molecular & General Genetics 185(2):245–50 (1982). Further, the eukaryote *Drosophila melanogaster* includes an inducible repair-recombination system in their female germ line.

Additional Mutagen Sensitive Genes

Suitable mutagen sensitive genes include a variety of genes whose activity is known to be inducible in the presence of or in response to mutagens. These include a dam gene; a mut gene, such as a mutD, a mutH, a mutL, or a mutS gene; a dna gene, such as a dnaB or a dnaQ gene; an uvr gene, such as an uvrA', an uvrC, an uvrD, or an uvrD252 gene; a gene for the sliding clamp subunit, or another subunit, of DNA polymerase III; a hex gene from *Streptococcus pneumoniae*; and the like. These genes, or homologous genes, can be found in *E. coli, S. typhimurium*, and additional microbes listed above for SOS genes. Such genes have been characterized and their sequences are known in the art. See: Kleinsteuber S. et al., Molecular & General Genetics 248(6):695–702 (1995); Quinones A. et al., Molecular & General Genetics 211(l):106–12 (1988); Martinez A. et al. J. Bacteriol. 179(16):5188–94 (1987); Siegel E. C. Molecular & General Genetics 191(3):397-400 (1983); and Prudhomme M. et al., J. Bacteriol. 173(22):7196–203 (1991). Suitable genes also include those essential during inducible mutagenesis. Such genes include polA (DNA polymerase I) and the genes for DNA ligase, glycosylases, and apurinic/apyrimidinic endonucleases. The present constructs and methods can also employ homologs of these genes as found in another bacterium or bacteriophage species.

Variant Mutagen Sensitive Gene

In addition to the native sequence mutagen sensitive gene described herein, it is contemplated that variants of the mutagen sensitive gene can be prepared. A variant mutant sensitive gene retains its sensitivity or responsiveness to mutagens. A variant mutagen sensitive gene can be prepared by introducing appropriate nucleotide changes into the native gene, or by synthesis of the variant gene. A preferred variant mutagen sensitive gene has at least about 80% nucleic acid sequence identity with, preferably at least about 85% nucleic acid sequence identity with, more preferably at least about 90% nucleic acid sequence identity with, even more preferably at least about 95% nucleic acid sequence identity with, and yet more preferably at least about 98% nucleic acid sequence identity with the naturally occurring or wild-type mutagen sensitive gene. Preferably, a variant mutagen sensitive gene hybridizes with the naturally occurring or wild-type mutagen sensitive gene under moderately stringent conditions, more preferably under stringent conditions. Preferably a variant mutagen sensitive gene includes codon and nucleotide substitutions that increase expression or responsiveness in the host cell. Those skilled in the art will appreciate that nucleotide or amino acid changes may alter processing and/or characteristics of the gene.

Variations in the native gene sequence can be made, for example, using various of the techniques known to a skilled worker. Variations can be a substitution, deletion or insertion of one or more nucleotides. Guidance in determining which nucleotides may be inserted, substituted or deleted without adversely affecting the desired mutagen response may be found by comparing the sequence the gene with that of homologous known genes and minimizing the number of changes made in regions of high homology. The variation allowed may be determined by systematically making insertions, deletions or substitutions of nucleotides in the sequence and testing the resulting variants for the desired mutagen response.

The variations can be made using methods known in the art such as oligonucleotide-mediated mutagenesis, PCR mutagenesis, transposon mutagenesis, mutD mutagenesis, and random chemical or radiation mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA*, 317:415 (1986)) or other known techniques can be performed on the cloned DNA to produce the variant DNA.

Fluorescent Protein

As used herein, "fluorescent protein" refers to any protein capable of fluorescing when excited with appropriate electromagnetic radiation. Fluorescent proteins include proteins having amino acid sequences that are either naturally occurring (wild-type) or variants of these sequences. The fluorescent protein of the invention can fluoresce by any of a variety of mechanisms. Preferably, the fluorescent protein does not require a cofactor or substrate. The fluorescent protein of the invention does not exhibit bioluminescence or chemiluminescence. A preferred fluorescent protein can be employed in a variety of cells.

A fluorescent protein can be isolated from nature or can be produced by recombinant or synthetic means. The term specifically encompasses naturally-occurring truncated or secreted forms of the fluorescent protein, naturally-occurring variant forms (e.g, alternatively spliced forms) and naturally-occurring allelic variants of the fluorescent protein.

Fluorescent protein can be measured by a device, such as a fluorimeter (e.g. a fluorometic microtiter plate reader with appropriate filters), a flow cytometer, or by epifluorescence microscopy. Methods for performing assays on fluorescent materials are well known in the art. A change in fluorescence refers to any change in absorption properties, such as wavelength and intensity, or any change in spectral properties of the emitted light, such as a change of wavelength, fluorescence lifetime, intensity or polarization. Typically, a change in fluorescence refers to a change in output of light.

Green Fluorescent Protein

Suitable fluorescent proteins according to the present invention include green fluorescent protein. As used herein, "green fluorescent protein" (GFP) refers to one of the class of proteins, typically from marine organisms, that emit green light when activated. Suitable green fluorescent proteins have been isolated and characterized from marine organisms such as the Pacific Northwest jellyfish, *Aequorea Victoria*, the sea pansy, *Renilla reniformis*, and *Phialidium gregarium*. A preferred green fluorescent protein, such as the GFP of Aequorea, can be employed in a variety of cells and requires no substrate to fluoresce. A transformed cell containing the green fluorescent protein fluoresces under various conditions, including when excited with blue light of about 450 nm to about 490 nm. See, e.g., Levine, L. D., et al., Comp. Biochem. Physiol., 72B:77–85 (1982); which is incorporated herein by reference for its disclosure of the structure and manipulation of *Phialidium gregarium* green fluorescent protein.

In a preferred embodiment, the green fluorescent protein is the GFP of the jellyfish *Aequorea Victoria* or a variant of this GFP. A variety of useful variants of Aequorea green fluorescent protein are known to those of skill in the art. These useful variants have been produced by modifying coding and amino acid sequences of the green fluorescent protein. Residues that can be varied to produce useful variants of Aequorea green fluorescent protein include one or more of the amino acids at positions: 26, 64, 65, 66, 68, 72, 73, 99, 100, 123, 127, 145, 146, 147, 148, 149, 153, 154, 163, 164, 167, 185, 202, 203, 208, 212, 235, and 238. Known substitutions at these residues the produce useful variants of Aequorea green fluorescent protein include one or more of: K26R, F64L, S65A, S65C, S65G, S65L, S65I, S65T, S65V, Y66H, Y66F, Y66W, V68L, S72A, S73P, F99S, F100S, I123V, K127E, Y145F, Y145H, N146I, N147Y, H148R, N149K, M153T, M154T, V163A, N164H, I167T, I167V, Q185R, S202F, T203I, T203L, T203Y, S208L, N212K, E235D, K238E, and K238N The variant green fluorescent proteins listed in this paragraph, and polynucleotides encoding them, can be employed in the methods and compositions of the invention.

Useful variants of green fluorescent protein include those in which at least one of positions 64, 68, or 72 is varied either individually or together with position 65. Useful substitutions at these positions include F64L, V68L, or S72A either individually or together with one of S65T, S65A, or S65G. Useful combinations include F64L and S65T; V68L, S72A, and S65A; and S72A and S65G. By way of further example, useful changes in the excitation and emission spectra of green fluorescent protein can be accomplished through single or combinations of amino acid substitutions including K26R, F64L, S65T, Y66W, N146I, M153T, V163A, N164H, and N212K; F64L and S65T; F64L, Y66H, and V163A; F64L, S65T, Y66H, and Y145F; F64L, S65C, I167T, and K238N; F64L, S65T, F99S, M153T, and V163A; F64L, S65T, F99S, M153T, V163A and S208L; F64L, S65T, Y66W N146I, M153T, V163A, and N212K; S65A; S65C; S65I; S65L; S65T; S65V; S65G, V68L, S72A, and T203Y; S65T; S65T, M153A, and K238E; S65T, S72A, N149K, M153T, and I167T; Y66H; Y66F; Y66W; Y66H and Y145F; Y66W, M153T, V163A, and N212K; Y66W, N146I, M153T, V163A, and N212K; Y66W, I123V, Y145H, H148R, M153T, V163A, and N212K; S72A, Y145F, and T203L; F99S, M153T, and V163A; F99S, M153T, V163A and S208L; I167V; I167T; and S202F and T203I. It is believed that residues 145–163 are beneficial locations for substitutions that can increase the fluorescence of the Aequorea green fluorescent protein. Additional useful changes in the excitation and emission spectra of green fluorescent protein result from combinations of amino acid substitutions such as S73P, F100S, K127E, N147Y, M154T, V164A, and E235D; F100S, M154T, V164A, Q185R, and E235D; and F100S, M154T, and V164A. The variant green fluorescent proteins listed in this paragraph, and polynucleotides encoding them, can be employed in the methods and compositions of the invention.

Amino acid substitutions reported in the art to have no detrimental effect on fluorescence by or other properties of the Aequorea green fluorescent protein include changing glutamine-80 to arginine; L3R; D76G; F99I; N105S; E115V; T225S; H231L, and L238E. It is believed that mutations of one or more of residues 76–115 will not adversely affect the function of the Aequorea green fluorescent protein. Further, inserting a valine residue as position 2 in a variant extended by one amino acid has no adverse effect on fluorescence. The variant green fluorescent proteins listed in this paragraph, and polynucleotides encoding them, can be employed in the methods and compositions of the invention.

Single amino acid substitutions that are detrimental to fluorescence intensity when made in the absence of other mutations include S65R, S65N, S65D, S65F, and S65W.

A variety of useful variants of Aequorea green fluorescent protein are described in U.S. Pat. Nos. 5,625,048, 5,804,287, and 5,998,204, PCT publication WO 96/23810, A. Crameri et al., Nature Biotech. 14, 315–319 (1996), and Cormack et al., Gene 173, 33 (1996); which are incorporated herein by reference for their disclosure of the structure and manipulation of green fluorescent proteins and polynucleotides that encode them. Such variants can be employed in the compositions and methods of the present invention. Methods for manipulating the coding sequence of the Aequorea green fluorescent protein, and plasmids including this sequence, are known in the art and are described in, for example, Matthysse, A. G., et al. FEMS Microbiology Letters, 145:87–94 (1996).

A variety of coding sequences for wild type and useful variants of Aequorea green fluorescent protein are commercially available, for example, from Clontech (Palo Alto, Calif.) and Quantum Biotechnologies (Montreal, Quebec, Canada). These suppliers provide the coding sequence in cloning and expression vectors. The coding sequences encode variants of green fluorescent protein that fluoresce blue, cyan, green, and yellow-green, and that can provide brighter fluorescence compared to the wild type protein. Such variants can be employed in the compositions and methods of the present invention.

Figure 4A:
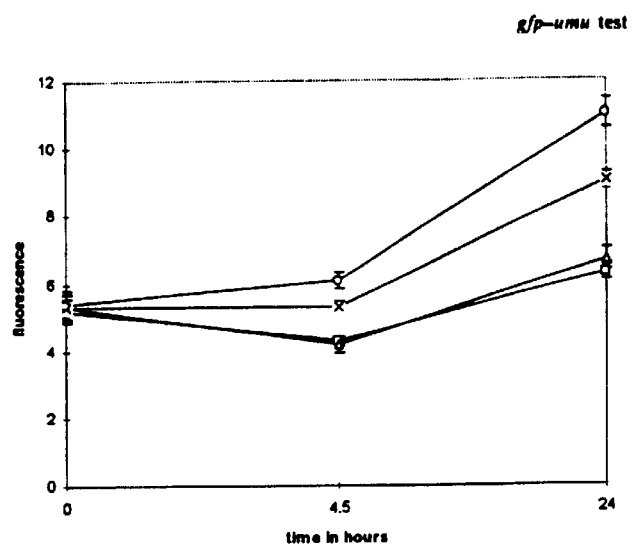
FIGS. 4a and 4b illustrate fluorescence of E. coli GW2100/pTJgfp versus time after 254 nm UV irradiation: (a) stationary phase cells; (b) logarithmic phase cells; □, 0 J/m$^2$ UV; ∆, 1 J/m$^2$ UV; X, 3 J/m$^2$ UV; O, 6 J/m$^2$ UV.

Suitable genes and coding sequences for wild type and variant green fluorescent proteins are described in Prasher et al., Gene 111, 229–233 (1992) and (GenBank Accession No. M62653) and in FIG. 4a of U.S. Pat. No. 5,958,713. The following sequences can provide a green fluorescent protein coding sequence for the DNA construct of the invention. The nucleotide and corresponding amino acid sequences for an A. Victoria green fluorescent protein have been reported by Prasher et al. supra with GenBank accession numbers M62654 (SEQ ID NO: 4 and SEQ ID NO: 5) and M62653 and by Inouye et al. (FEBS Lett 351(2–3): 277–280 (1994)) with GenBank accession number L29345. The nucleotide and corresponding amino acid sequences for an A. Victoria green fluorescent protein mutant 3 have been reported by Cormack et al. (Gene supra and Microbiology 143(Part 2):303–11 (1997)) and given GenBank accession number U73901 (SEQ ID NO: 23 and SEQ ID NO: 24). The disclosures of each of the GenBank accessions mentioned in this paragraph are incorporated herein by reference.

A preferred *Aequorea Victoria* green fluorescent protein is the variant encoded by a polynucleotide having the sequence shown in FIG. 14 (SEQ ID NO: 6), or a degenerate sequence encoding the same amino acid sequence. A preferred degenerate sequence employs codons optimized for expression in the host cell. The amino acid sequence of the preferred green fluorescent protein is also illustrated in FIG. 14 (SEQ ID NO: 7). This sequence has been reported as mut2 by Cormack et al. Gene (1996). A portion of this sequence can be PCR amplified using the method of Matthysse et al (1996) using primers such as gfpHindIII-F (5'-CTCAAGCTTGATTTCTAGATTTAAGAAGG) (SEQ ID NO: 8) and gfpEcoRi-R (5'-CTCGAATTCTCATTATTTGTATAGTTCATCCATGCC) (SEQ ID NO: 9) to generate a 740 base pair product.

Additional Fluorescent Proteins

Other fluorescent proteins can be used in the compositions and methods of the present invention. For example, the fluorescent protein of the invention can be a blue fluorescent protein, which is one of the class of proteins, typically from marine organisms, that emit blue green light when activated. Clontech (Palo Alto, Calif.) provides cloning and expression vectors encoding a suitable red fluorescent protein found in the IndoPacific sea anemone relative Discosoma species. The methods and compositions of the invention can also employ yellow fluorescent protein from *Vibrio fischeri* strain Y-1, phycobiliproteins from marine cyanobacteria such as Synechococcus, e.g., phycoerythrin and phycocyanin, oat phytochromes from oat reconstructed with phycoerythrobilin, or *Propionibacterium freudenreich* uroporphyrinogen III methyltransferase (cobA) gene product. These fluorescent proteins have been described in Baldwin, T. O., et al., Biochemistry 29:5509–5515 (1990); and Wilbanks, S. M., et al., J. Biol. Chem. 268:1226–1235 (1993); which are incorporated herein by reference for their disclosure of the structure and manipulation of fluorescent proteins and polynucleotides that encode them. See also Li et al., Biochemistry 34:7923–7930 (1995) and Wildt S. et al. Nature Biotechnology 17(12):1175–1178 (1999).

Variant Fluorescent Protein

In addition to the full-length native sequence fluorescent protein described herein, it is contemplated that fluorescent protein variants can be employed in the invention. Variant fluorescent proteins remain fluorescent proteins. A "variant" fluorescent protein has at least about 80% amino acid sequence identity with a wild type fluorescent protein. For example, a sequence identity of a variant green fluorescent protein can be compared to a green fluorescent protein having the wild type amino acid sequence, which is known in the art. Such fluorescent protein variants include, for instance, fluorescent proteins wherein one or more amino acid residues are added, or deleted, at the N- or C-terminus, or internally in the sequence. Ordinarily, a fluorescent protein variant will have at least about 80% amino acid sequence identity, preferably at least about 85% amino acid sequence identity, more preferably at least about 90% amino acid sequence identity, even more preferably at least about 95% amino acid sequence identity and yet more preferably 98% amino acid sequence identity with the wild type fluorescent protein.

Fluorescent protein variants can be prepared by introducing appropriate nucleotide changes into the fluorescent protein-encoding DNA, or by synthesis of the desired fluorescent protein. Those skilled in the art will appreciate that amino acid changes may alter processing or characteristics of the fluorescent protein.

Variations in the native full-length sequence fluorescent protein, can be made, for example, using any of the techniques and guidelines for conservative and non-conservative mutations set forth, for instance, in U.S. Pat. No. 5,364,934. Variations may be a substitution, deletion or insertion of one or more codons encoding the fluorescent protein that results in a change in the amino acid sequence of the fluorescent protein as compared with the native sequence fluorescent protein. The variant can also include codons optimized for the host cell. Guidance in determining which amino acid residue may be inserted, substituted or deleted without adversely affecting the fluorescence, or other desired activity, of the fluorescent protein may be found by comparing the sequence of the fluorescent protein with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for fluorescence, or other desired activity, of the fluorescent protein variant.

The variations can be made using methods known in the art such as oligonucleotide-mediated mutagenesis, PCR mutagenesis, transposon mutagenesis, mutD mutagenesis, and random chemical or radiation mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA*, 317:415 (1986)) or other known techniques can be performed on the cloned DNA to produce the fluorescent protein-encoding variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W. H. Freeman & Co., N.Y.); Chothia, *J. Mol. Biol.*, 150:1 (1976)). If alanine substitution does not yield adequate amounts of variant, an isosteric amino acid can be used.

The coding sequence of a wild-type or variant fluorescent protein, such as green fluorescent protein, can be concatenated with those encoding many other proteins; the resulting in a variant fluorescent protein that is a fusion protein. Such fusion proteins typically fluoresce and retain the biochemical features of the partner proteins. See, e.g. Cubitt, A. B., et al., Trends Biochem. Sci. 20:448–455 (1995).

The variant fluorescent protein can also include a localization sequence to direct the indicator to particular cellular sites by fusion to appropriate organellar targeting signals or localized host proteins. A polynucleotide encoding a localization sequence, or signal sequence, can be ligated or fused at the 5' terminus of a polynucleotide encoding the fluorescence indicator such that the signal peptide is located at the amino terminal end of the resulting fusion polynucleotide or polypeptide. In the case of eukaryotes, the signal peptide is believed to function to transport the fusion polypeptide across the endoplasmic reticulum. The secretory protein is then transported through the Golgi apparatus, into secretory vesicles and into the extracellular space or the external environment. Signal peptides which can be utilized according to the invention include pre-pro peptides which contain a proteolytic enzyme recognition site. Other signal peptides are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", chapter 35 of Stryer, L., Biochemistry (4th ed.). W. H. Freeman, 1995. The localization sequence can also be a localized protein.

DNA Construct

The present invention includes a DNA construct with expression of a fluorescent protein operably linked to, an SOS, or other mutagen sensitive, gene. The DNA construct can be a plasmid or other expression vector. Typically, a regulatory region of a mutagen sensitive gene is fused to the coding sequence of a fluorescent protein. Methods for producing, and the structures of, regulatory regions of genes fused to coding sequences are known in the art or can be routinely developed by a skilled worker. For example, a DNA molecule encoding a fluorescent protein, which can be made by PCR, can be ligated to a restriction fragment of a plasmid, vector, or other DNA molecule encoding a mutagen sensitive gene, such as an SOS gene. The coding sequence for the fluorescent protein is positioned so its expression is operatively controlled by the mutagen sensitive gene.

A preferred embodiment of the DNA construct of the invention includes a regulatory region of an SOS gene, such as a promoter of a umuDC operon of *E. coli*, fused to the coding sequence of a green fluorescent protein, such as the green fluorescent protein from Aequorea. The this can be accomplished by ligating a PCR fragment encoding a green fluorescent protein to a restriction fragment of a plasmid encoding a umu operon promoter, and all or part of the coding sequences for the umuD gene and/or the umuC gene. A preferred plasmid is plasmid pSE 117; Marsh, G. C., et al., J. Bacteriol. 162:155–161 (1985), the disclosure of which is incorporated herein by reference.

FIG. 15 illustrates another preferred plasmid, pTJgfp. The plasmid includes a preferred umuDC gene (SEQ ID NO: 1) and a coding sequence for a preferred variant green fluorescent protein (SEQ ID NO: 6). It also includes a colE1 replication origin, ori, and a Bla coding sequence for a ∂-lactamase selectable marker. The structure and construction of pTJgfp are described in the Examples below and illustrated in FIG. 15.

The DNA construct typically contains a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. A preferred selectable marker is a beta-lactamase gene, which provides ampicillin resistance. A variety of selectable markers known to those of skill the art can be routinely employed in the present DNA construct.

The present construct can, alternatively, employ a replicon based on an origin of replication other than ColE1. This is particularly advantageous for making a host cell with more than one construct of the present invention. Two plasmids with the same replication origin cannot be stably maintained in the same cell, since, for example, the enzymatic machinery of the cell does not recognise them as being different and hence all of the copies of both will not necessarily partition evenly into two groups during cell division. Thus, when more than one construct of the invention is employed in a host cell, they must include different origins of replication. Origins of replication different from ColE1 are known in the art and include RP4, R100, pSC101, R6K. Further, a plasmid with an origin of replication different from ColE1 can be advantageous in combination with certain mutagen sensitive DNA polymerase genes. Certain of these genes, such as polA genes, are unstable in ColE1 vectors.

For use in mammalian cells, a construct of the invention, or a second construct in the host cell, can advantageously encode a gene product that can simulate mammalian metabolism, such as a mammalian P450 mixed function oxidase.

Host Cell

A host cell is a cell in which a mutagen sensitive gene can cause production of a fluorescent protein in response to a mutagen. This can be accomplished by a variety of different cells, for example prokaryotic cells and eukaryotic (e.g. mammalian) cells, or cells of single or multi-cellular organisms. Preferably, the host cell is a prokaryotic cell, preferably a bacterial cell. The host cell is suitable for expression and induction of the DNA construct. Suitable host cells include Enterobacteriaceae (e.g. Shigella, Salmonella, Escherichia, Proteus, Erwinia and the like) and gram positive bacteria (e.g. Bacillus, Streptococcus, Staphylococcus, the Actinomycetes, and the like). Preferred host cells include a cell in which an SOS, or other mutagen sensitive, gene can be expressed when the host cell's DNA is damaged by a mutagen. A preferred host cell is a microbe, preferably a bacterium, subject to or capable of an SOS response.

Preferred bacteria host cells include *Escherichia coli*, such as an *E. coli* K12, B or B/r strain; and including *E. coli* strains AB1157, DB6659, GW2100, DH5, CC118, CSH26; and the like. Preferred bacteria host cells include *Salmonella typhimurium*, such as the *S. typhimurium* LT2 subline strains developed in the Ames lab at Berkeley, e.g. TA1535, TA1537, TA1537, TA1538, TA98, TA100, TA102 and subsequent variations or improvements of them; a *S. typhimurium* strain from the LT2 or LT22 sublines; a *S. typhimurium* strain NM1011, NM2009, NM5004, NM6001, NM6002, or OY100/1A2; and the like. Certain strains of *Saccharomyces cerevisiae, Schizosaccharomyces pombe, Bacillus subtilis, Neurospora crassa*, or *Pseudomonas aeuroginosa* can also be employed as host cells to carry a variety of the plasmid variants as previously described.

Suitable host cell strains are described in Walker (1984), supra; Marsh, G. C., et al. (1985) supra; Herrerro, M., et al. J. Bacteriol. 172:6557–6567 (1990); Justus, T. and Thomas, S. M. Mutation Res. 398: 131–141 (1998); and Justus, T. and Thomas, S. M. Mutagenesis 14(4):351–356 (1999); which are incorporated herein by reference for their disclosure of characteristics and manipulation of these host cell strains. See also, Miller, J. H., Experiments in Molecular Genetics, Cold Spring Harbor Laboratory, 1972; Oda Y. et al. Mutation Research 334(2):145–56 (1995); Oda Y. et al. Mutation Research 272(2):91–9 (1992); Aryal P. et al. Mutation Research-Genetic Toxicology & Environmental Mutagenesis 442(2):113–120 (1999); Oda Y. et al. Carcinogenesis 20(6):1079–1083 (1999); Oda Y. Carcinogenesis 17(2):297–302 (1996); and Schmid C. et al. Mutation Research-Genetic Toxicology & Environmental Mutagenesis 394 (1–3):9–16 (1997).

A host cell may be cultured under standard conditions of temperature, incubation time, optical density, plating density and media composition corresponding to the nutritional and physiological requirements of the host cell. However, conditions for maintenance and growth of the host cell may be different from those for assaying candidate mutagens in the methods of the invention. Modified culture conditions and media can be used to facilitate detection of the expression of a fluorescent protein or an SOS response.

Host cell strains, cultures, or cell lines may be expanded, stored, or retrieved by a variety of techniques known in the art and appropriate to the host cell. For example, a host cell of the invention can be preserved by stab culture, plate culture, or in glycerol suspensions and cryopreserved in a freezer (at –20.degree. C. to –100.degree. C.) or under liquid nitrogen (–176.degree. C. to –196.degree. C.).

Selection and Transformation of Host Cells

Host cells are transfected or transformed with a DNA construct described herein for mutagen detection, an SOS response, or fluorescent protein expression and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in Hanahan, D. (1985) Techniques for transformation of *E coli*; In Glover, D. M. (ed) "DNA Cloning Vol 1: a practical approach", IRL Press, Oxford, UK, pp109–135. A standard method for the transformation of plasmids into *E coli* uses cold calcium chloride. Greater competence can also be generated through the use of more involved protocols known in the art and employing rubidium chloride or hexamine cobalt chloride.

Additional methods of transfection are known to the ordinarily skilled artisan, for example, $CaPO_4$ treatment and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers.

Infection with *Agrobacterium tumefaciens* is used for transformation of certain plant cells, as described by Shaw et al., Gene, 23: 315 (1983) and WO 89/05859 published Jun. 29, 1989. For mammalian cells without such cell walls, the calcium phosphate precipitation method of Graham and van der Eb, Virology, 52:456–457 (1978) can be employed. General aspects of mammalian cell host system transformations have been described in U.S. Pat. No. 4,399,216. Transformations into yeast are typically carried out according to the method of Van Solingen et al., J. Bact., 130: 946 (1977) and Hsiao et al., Proc. Natl. Acad. Sci. (USA), 76: 3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et aL, Methods in Enzymology, 185: 527–537 (1990) and Mansour et al., Nature, 336: 348–352 (1988).

Detecting Gene Amplification/Expression

A host cell which contains a sequence encoding a fluorescent protein or an SOS gene and which express the fluorescent protein or the SOS gene may be identified by a variety of known methods. For example the host cell can be assayed for the presence or absence of "marker" gene functions (e.g., resistance to antibiotics) or detection of fluorescent protein by, for example, its fluorescence (e.g. detection of fluorescence by epifluorescence microscopy). Gene amplification and/or expression may be measured in a sample directly, for example, by conventional Southern blotting, Northern blotting to quantitate the transcription of MRNA (Thomas, Proc. Natl. Acad. Sci. USA, 77:5201–5205 (1980)), dot blotting (DNA analysis), in situ hybridization, using an appropriately labeled probe, or PCR based on appropriate primers, based on the sequences described herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal.

Detecting Mutagens

A mutagen can be detected by incubating a host cell in a suitable nutrient medium, such as nutrient broth or on nutrient agar. The nutrient medium can include a suitable selection reagent, such as an antibiotic, to select for host cells including a DNA construct of the invention. Stationary phase host cells can be obtained by growing the cells for a prolonged period, such as overnight. Logarithmic phase host cells can be obtained by diluting stationary cultures and incubating them again before use for detecting a mutagen.

For example, logarithmic phase cells can be obtained by diluting overnight cultures cells 1:10 and regrowing them for two hours at 37° C. before use.

For testing a chemical mutagen, a test compound is added to a host cell culture and the cell culture is incubated for a time suitable for appearance of a fluorescent signal in the presence of a mutagen. In a preferred embodiment, the amount of a test compound added to a cell culture does not adversely effect culture conditions for growth of the host cell. For example, about 0.01 to about 0.1 ml of a test compound solution can be added to about 2 ml of a host cell culture. Alternatively, in an embodiment preferred for detecting weak mutagens or mutagens in an environmental sample, sufficient nutrient media can be displaced or replaced by test compound that the host cell is deprived of nutrient to some degree, or even starved.

During treatment with mutagen, the cells can be maintained either at stationary or logarithmic phase. Preferably, if cells are deprived of nutrients or starved, they are maintained at logarithmic phase during exposure to mutagen. A host cell can be incubated with a mutagen for a time as short as 1 or 2 hours or as long as about 24 or 48 hours, or longer. Preferred incubation times include about 4.5 to about 24 hours. Advantageously, stability of the fluorescence produced by a fluorescent protein, such as green fluorescent protein, allows the present method to be conducted with incubations longer than can be achieved with previous systems that detect mutagens by producing light or a visible signal.

After treatment with mutagen, the cells can be diluted with nutrient medium and incubated for the detection of mutagenesis. For example, a 2 ml mutagen treated host cell sample can be diluted with 18 ml of nutrient medium. The host diluted cells are incubated under conditions suitable for expression of the fluorescent protein. For example, the diluted host cells can be dispensed at 0.15 ml/well into 96 well microtiter plates and incubated at 37° C. Alternatively, a sufficient number of cells to start a new culture can be removed from the mutagen treatment mixture and used to inoculate an aliquot of nutrient medium. For example, about 10 to about 50 cells can be employed to inoculate a 0.15 ml culture in a microtiter plate. The plate and cells can then be incubated at 37° C.

After the host cells have been grown under conditions suitable for expression of the fluorescent protein, fluorescence can be monitored using any suitable apparatus, several of which are listed above. For example, fluorescence can be monitored by employing a fluorescence microtiter plate reader with the mission and excitation wavelengths selected for the fluorescent protein. Green fluorescent protein can be detected with an emission wavelength of about 510 or about 520 nm and an excitation wavelength of about 485 nm. Appropriate excitation and emission wavelengths for existing variant green fluorescent proteins are known in the art. An increase in fluorescence output, level, or distribution compared to a suitable control indicates that a test compound is a mutagen. Fluorescence can be read directly and/or automatically from the culture of host cells, which provides an advantage in steps, time, materials, and cell handling compared to previous methods that require culturing revertant colonies, and like methods.

A mutagen typically produces a dose dependent increase in fluorescence, although low levels of some mutagens may not produce an increase that is apparent without statistical analysis. Similarly, some mutagens may require a longer or shorter time than others to produce a significant or dose dependent increase.

Suitable nutrient growth media for bacteria that can be employed during incubation to detect mutagens include nutrient broth, Luria broth, defined minimal media, such as Vogel-Bonner or Davis-Mingoli salts.

Detecting Antimutagens

Antimutagens are agents that lower a mutation rate. They have potential as therapeutic agents to control proliferative conditions in individuals affected by DNA repair deficiencies. Their detection is problematic in conventional assays that rely on the detection of a lowering of mutant colony counts in assays such as the Ames test. The present construct and host cell can test for antimutagens that, when added to cultures of host cells containing the present construct, lower fluorescent output. For example, the cells can be exposed to both a mutagen and an antimutagen simultaneously, and the fluorescent output is lower than from cells exposed only to the mutagen. A concurrent toxicity assay can check that the decrease in fluorescence was not due to cell death.

Toxicity Assays

When testing mutagens or antimutagens, a toxicity assay can be run concurrently, on the same or different cells. A toxicity assay can provide a suitable control to account for any decrease in fluorescence that might be due to general toxicity to the host cells.

Statistical Analysis

The present DNA construct, host cell, and methods can be employed to a detecting mutagen solely on the basis of an increase in the level of fluorescent protein expression or detected fluorescence compared to a suitable control. Statistical analysis of the location, distribution, amount, pattern, or the like of fluorescent protein can be conducted on replicate mutant treated samples. For example, under conditions where there is no significant difference between the arithmetic mean of samples, statistical analysis of the distribution of fluorescence can detect a mutagen.

For accomplishing such a statistical analysis in standard assays such as the Ames test, multiple replicate cultures (either in the presence or absence of a mutagen) can be grown and a sample of each analysed to see how many mutants it contains (as measured by a plating assay for mutant colonies). The resulting mathematical distribution describes the numbers of mutants in many cultures. Changes in the shape of the distribution or its placement measure far subtler changes in mutation rate than a simple shift in the arithmetic mean. However, analyses of this type are employed infrequently due to their technical difficulty A fluorescent protein, such as green fluorescent protein can be employed in an assay of this type to determine changes in the shape or placement of a mutant distribution from replicate cultures without increasing the technical difficulty of the experiment. Interestingly, the fluorescence output of any individual culture carrying a mutagen sensitive gene operably linked to a fluorescent protein may not correlate with the number of mutants in that culture, since transcription of a single fused gene need not mirror the whole DNA repair capacity of a growing culture. However, a stable fluorescent signal, such as that from green fluorescent protein provides a cumulative record of transcription of a single fused gene, and indicates how this varies between replicate cultures. Significantly, this type of analysis does not work with the lux reporter. Thus, the present construct can be used to detect subtle mutagens that otherwise might be missed in conventional assays, as well as more potent ones.

In one embodiment, the Kolmogorov-Smirnov Z Test (KZ test) can be employed to detect differences in both the locations and shapes of fluorescence distributions. This test is well characterized for analysis of variable locations, shapes, and distributions of data. A significant difference between a control and a test compound according to the Kolmogorov-Smirnov Z test indicates that the test compound is a mutagen. A significant difference can be denoted by a P value of less than about 0.1, preferably less than about 0.05. The Kolgomogorov-Smirnov Z test can be applied according to the SPSS statistical analysis software package, version 7.5. The SPSS software package also includes the Mann-Whitney test, which can illustrate the differences in distribution.

The present invention may be better understood with reference to the following examples. These examples are intended to be representative of specific embodiments of the invention, and are not intended as limiting the scope of the invention.

EXAMPLES

Example 1

Transcriptional Fusions of Green Fluorescent Protein as Reporters of Bacterial Mutagenesis A fluorescent protein under control of a mutagen sensitive gene produces a robust and dose-dependent response to mutagens.

Materials and Methods

Bacterial strains and plasmids. Bacterial strains and plasmids used in these examples are listed in Table 1.

TABLE 1

Bacterial strains used in this study

| Strain | Relevant characteristics | Source/reference |
|---|---|---|
| E. coli GW2100 | AB1157 umuC::Tn5 | G. Walker |
| E. coli DH5/pSE177 | recA hsdR$_{EcoK}$/pSE117 | Marsh and Walker (1985) |
| E. coli GW2100/pTJ10 | AB1157 umuC::Tn5/pTJ10 (umuC'::luxAB) | Justus and Thomas (1998) |
| E. coli GW2100/pTJgfp | AB1157 umuC::Tn5/pTJgfp (umuC'::gfp) | This example |
| S. typhimurium TA1537 | HisC3076Δ (gal uvrB bio) rfa | B. N. Ames via D. G. MacPhee |
| S. typhimurium TA1537/pTJ10 | HisC3076Δ (gal uvrB bio) rfa/TJ10 (umuC'::luxAB) | This example |

Media and growth conditions. Bacteria were grown in nutrient broth (Oxoid CM1) or on nutrient agar (Oxoid CM3), both supplemented with the addition of 50 µg/ml ampicillin (Sigma A951), and shaken at 200 r.p.m. at 27° C.

DNA cloning. Methods for plasmid DNA isolation, restriction endonuclease digests, DNA ligation, alkaline phosphatase treatment and agarose gel electrophoresis techniques followed standard protocols. Cells were transformed by standard methods with the following modifications: cells were heat shocked at 37° C. for 10 min and then grown in nutrient broth. DNA was isolated from agarose using agarase from Pseudomonas atlantica according to the manufacturer's instructions (Boehringer Mannheim).

PCR. PCR amplification of the gfp gene sequence was conducted as described by Matthysse et al., FEMS Microbiol. Lett. 145:87–94 (1996), the disclosure of which is incorporated herein by reference for disclosure of PCR and microscopy methods.

umuC-gfp gene fusion construction. The 700 bp gfp PCR fragment was ligated to a 7 kb HindIII-EcoRI fragment from plasmid pSE 117 (FIG. 1). *Escherichia coli* GW2100 cells were transformed with this ligation mixture and transformants selected on nutrient agar with ampicillin.

gfp-umuC gene fusion confirmation. Plasmid preparations of colonies that resulted from ligation were PCR amplified using gfp primers to confirm the presence of the gfp gene (data not shown). Colonies were also screened for fluorescence using epifluorescence microscopy.

Fluorescent detection methods. Stationary phase cells were obtained for experiments by allowing cells to grow up overnight. Logarithmic phase cells were obtained by diluting overnight culture cells 1:10 and regrowing them for 2 h at 37° C. prior to use in experiments. During fluorescent assays bacterial cell culture in either logarithmic phase or stationary phase (2 ml) were with incubated for a predetermined time with mutagen, and then added to 18 ml of nutrient broth or 0.85% saline with ampicillin. For UV-irradiated cells this involved irradiating cells in Falcon 60×15 mm tissue culture dishes with regular stirring. All other mutagens were added to this 2 ml of cells. This mixture was then dispensed at 150 µl/well into 96 Uniwell microtiter plates (Elkay) and incubated at 37° C. with shaking. Fluorescence was measured using a Fluoroskan Ascent by Labsystems using the Ascent computer software package v.2.2, with an emission filter of 510 nm and excitation filter of 485 nm. Measurements were taken for three incubation times with mutagen; time 1 being fluorescence prior to incubation, time 2 at 4.5 h, and time 3 at 24 h. All fluorescent values are presented as the means (error bars show standard deviations) of 96 cultures grown in parallel to obtain a statistically more accurate representation of mutation rate.

Results

Figure 2A:
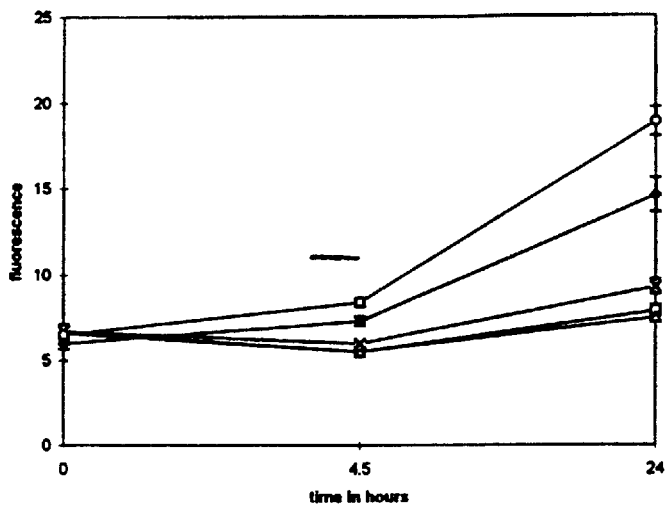
FIGS. 2a and 2b illustrate fluorescence of E. coli GW2100/pTJgfp versus time following treatment with N-methyl-N-nitro-N-nitrosoguanidine (MNNG): (a) stationary phase cells; (b) logarithmic phase cells;□, 0 µg/ml MNNG; ∆, 0.1 µg/ml MNNG; X, 1.5 µg/ml MNNG; ♦.3.5 µg/ml MNNG; O, 7 µg/ml MNNG.
Figure 2B:
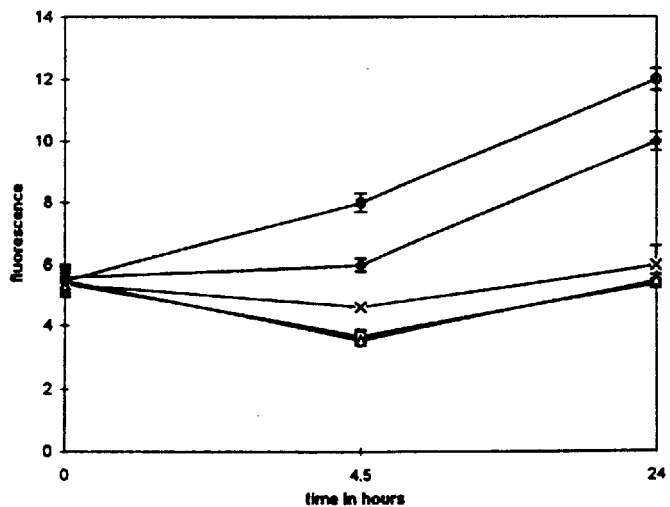
Figure 3A:
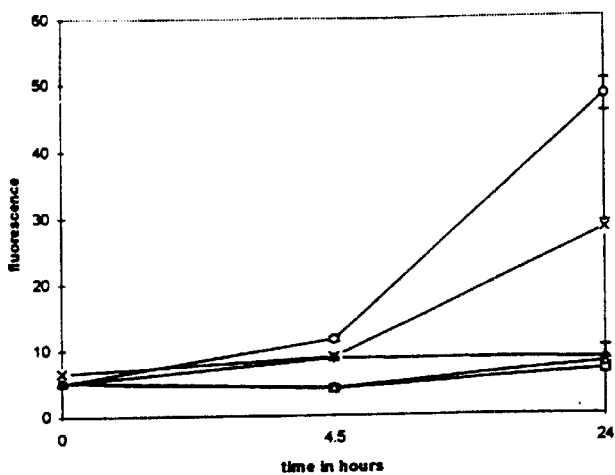
FIGS. 3a and 3b illustrate fluorescence of E. coli GW2100/pTJgfp versus time following treatment with methylmethane sulphonate (MMS): (a) stationary phase cells; (b) logarithmic phase cells; □, 0 pg/ml MMS; ∆, 13 µg/ml; X, 325 µg/ml; O, 650 µg/ml; ♦, 1300 µg/ml.
Figure 3B:
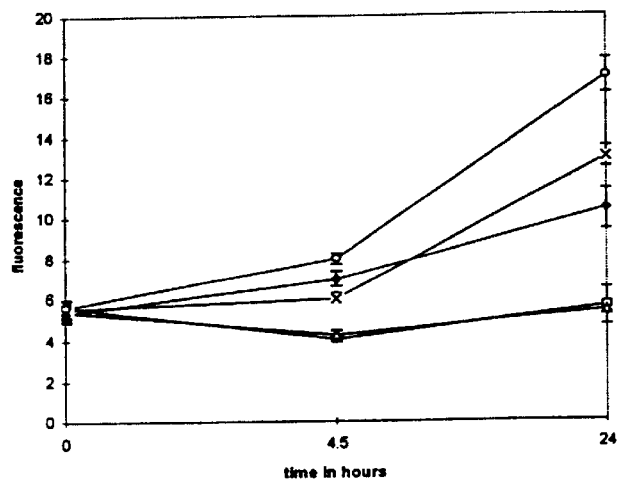
Figure 4B:
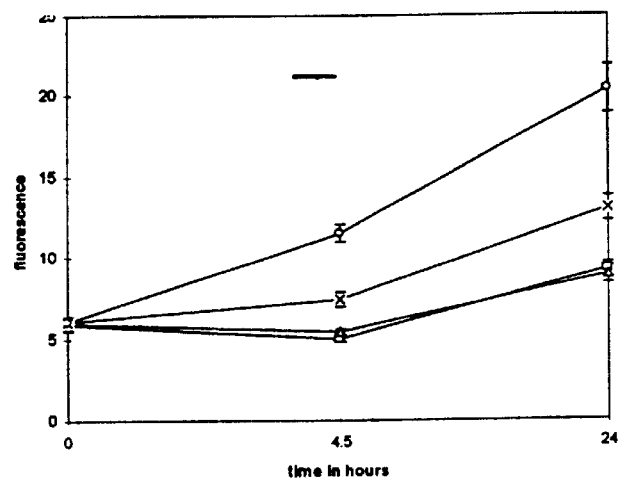

Cultures in both logarithmic and stationary growth phases were tested following mutagen treatment (FIGS. 2–4). The fluorescent signal from stationary phase cells did not differ significantly from those in logarithmic phase (FIGS. 2–4). The chemical mutagen N-methyl-N-nitro-N-nitrosoguanidine (MNNG) induced a dose-dependent increase in fluorescence levels at 1.5, 3.5 and 7 µg/ml (FIG. 2). In this study, there was no significant increase in fluorescence level at 0.1 µg/ml when compared with the 0 dose control (FIG. 2). When another chemical mutagen, methylmethane sulphonate (MMS), was assayed cells showed no significant difference in fluorescence level from the 0 dose control and 13 µg/ml MMS, but they responded in a dose-dependent manner at 325 and 650 µg/ml (FIG. 3). At a higher dose of 1300 µg/ml a lower level of fluorescence was observed, most likely due to cellular toxicity (FIG. 3). The physical mutagen UV irradiation failed to induce a significant difference in fluorescence level from the 0 dose control at 1 J/M$^2$, but at 3 and 6 J/M$^2$ a dose-dependent increase in fluorescence level was seen (FIG. 4).

Figure 5:
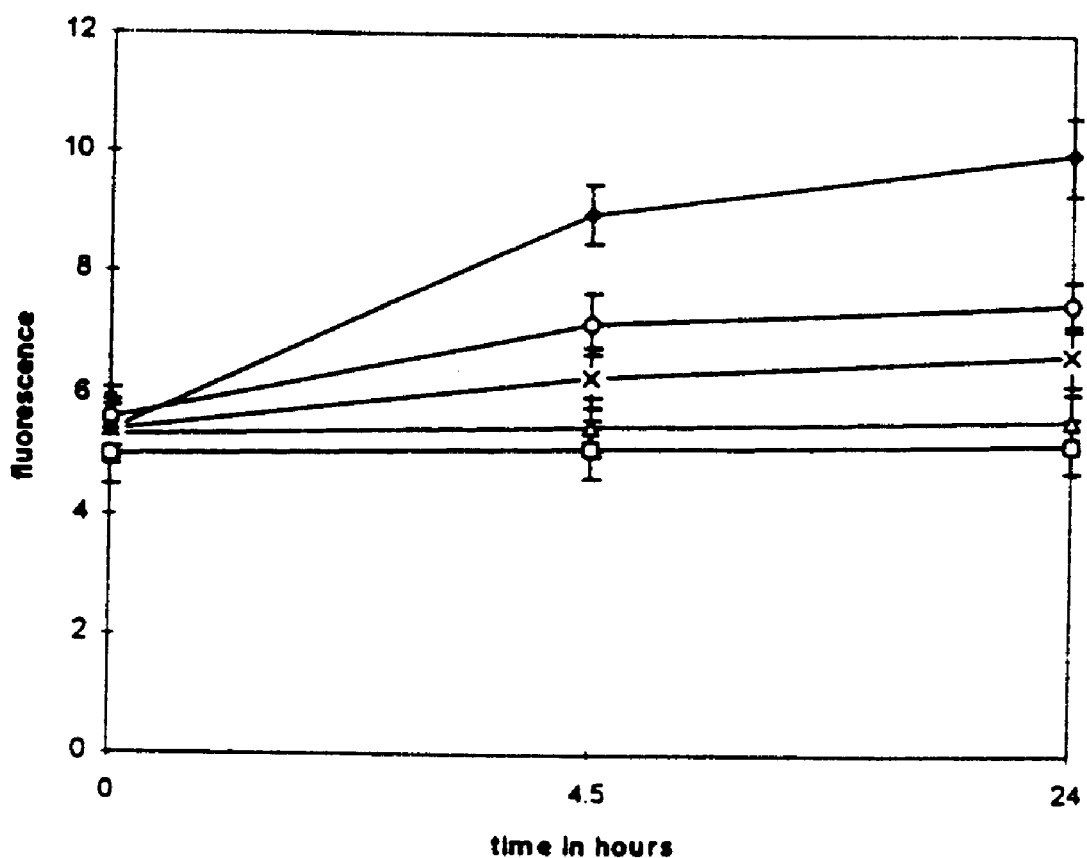
FIG. 5 illustrates fluorescence of E. coli GW2100/pTJgfp cells in logarithmic phase versus time following treatment with MNNG in 0.85% saline: □, 0 µg/ml MNNG; ∆, 0.1 µg/ml MNNG; X, 1.5 µg/ml MNNG; O, 3.5 µg/ml MNNG; ♦, 7 µg/ml MNNG.
Figure 6:
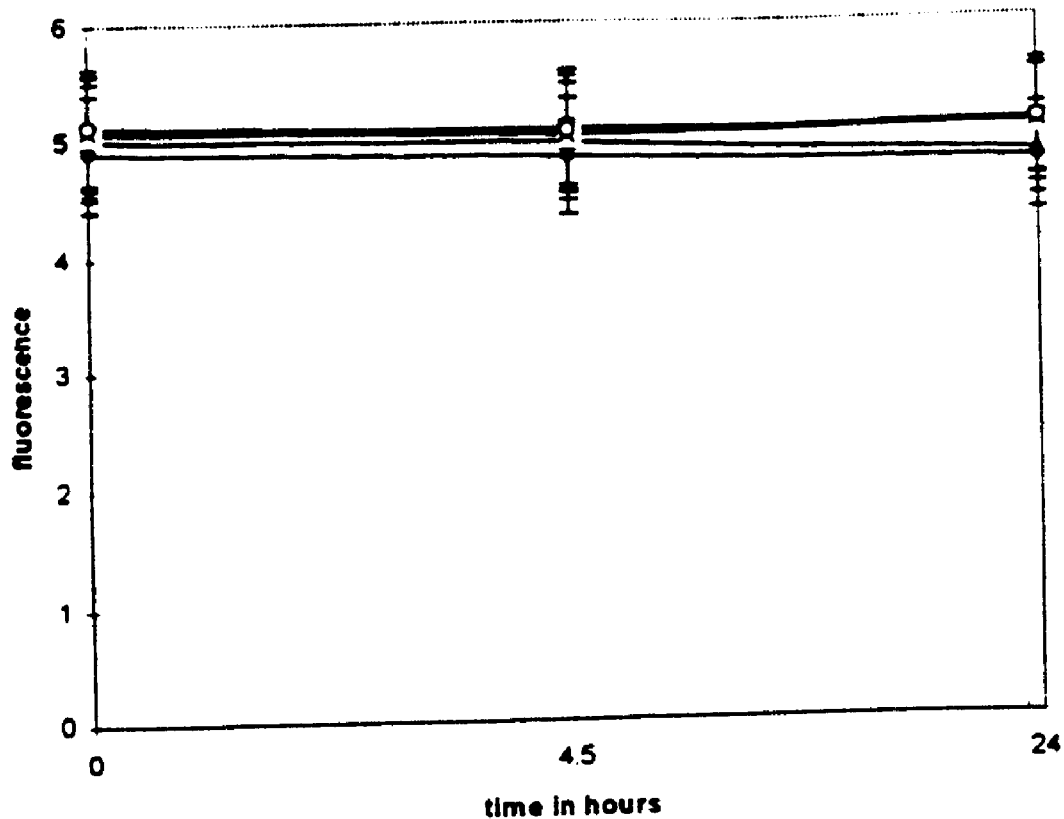
FIG. 6 illustrates fluorescence of E. coli GW2100/pTJgfp cells in stationary phase versus time following treatment with MNNG in 0.85% saline: □, 0 µg/ml MNNG; ∆, 0.1 µg/ml MNNG; X, 1.5 µg/ml MNNG; ♦, 3.5 µg/ml MNNG; O, 7 µg/ml MNNG.

When assays were conducted over periods of time up to 24 h the signal from the gfp reporter system increased with time whilst there was a marked decrease in lux-derived luminescence (FIGS. 2–4). This demonstrates the more robust nature of the gfp system compared with lux, which is very dependent on cell physiology at the immediate time of assay due to its shorter half-life. gfp is thus more suitable than the luciferase system for a variety of assays, including those where the mutagen dose being assayed is comparatively high and/or a rapid result is not crucial.

gfp gene expression cells were assayed in 0.85% saline. The results shown in FIGS. 5 and 6 indicate that cells do not require cultivation in a nutrient-rich medium for a dose-dependent response to a mutagen to occur. However, there is the requirement that cells be in logarithmic phase (FIG. 5) and not a stationary phase (FIG. 6) for reporter gene induction to occur in saline.

Discussion

Previous work has shown that the luxA and luxB (luciferase) genes from Vibrio harveyi can be successfully fused to bacterial DNA repair genes to provide a sensitive and semi-quantitative assay for the presence of a mutagen. One drawback with this luciferase system, however, is the need for cells to be in a metabolically active state, together with the transient state of the luminescent signal that begins to decline after 24 h. This means that for the test to be useful samples would need to be processed in the laboratory under quite invariant conditions.

A distinct advantage of the gfp system though does appear to be the robust and long lasting nature of the signal. When cells carrying either reporter construct were left in the presence of mutagens for 24 h before reading, fluorescent signals could still be detected easily, whereas luminescence was not. Thus gfp-based testing can be employed under conditions where extended exposure to mutagenic agents is required.

The gfp-based reporter system showed no detectable variation in response when using cells from different growth phases in nutrient broth, unlike the lux system. Dose-dependent increases in fluorescence were observed for each of the mutagens tested. However, when cells were starved, induced fluorescence was only seen in logarithmic phase cells. This is another advantage of the gfp reporter system compared with the lux. As a result, green fluorescent protein may be a more suitable reporter for detection of high levels of mutagens in environmental samples, as often nutrient levels in such samples may be low.

Example 2

Transcriptional Fusions of Green Fluorescent Protein for Detecting Weak Mutagens A fluorescent protein under control of a mutagen sensitive gene produces a robust and dose-dependent response to weak mutagens and low concentrations of mutagens.

Materials and Methods

Bacterial strains and plasmids. The bacterial strain used in this study was E. coli GW2100/pTJgfp, the details of which are described above in Example 1. Plasmid pTJgfp contains a transcriptional fusion between the promoter of the umuC DNA repair gene of E. coli, and the gfp fluorescence gene of Aqueorea Victoria. It has been shown in Example 1 to confer on cells the ability to emit light when challenged with DNA damaging agents. GW2100 is a derivative of the standard AB 1157 strain in which transposon Tn5 insertion has inactivated the chromosomal umuC gene.

Detection of mutation from arg-3 to Arg$^+$ using colony assays. Cultures of E. coli were grown overnight in Nutrient Broth (Oxoid Code CM1) at 37° C., shaking at 200 rpm. The resultant stationary phase cultures were diluted by $10^8$ and, where appropriate, mutagens were added. 150 $\mu$l aliquots of the diluted cultures were then added to each of 24 or 48 microtiter plate wells and incubated at 37° C. overnight. Following incubation a 100 $\mu$l sample was removed from each well and plated onto Davis Mingioli Minimal O Medium, supplemented with 50 $\mu$l histidine, proline, leucine and threonine, 5 $\mu$l/ml thiamine, and with glucose (1%w/v) present as a sole carbon source. Plates were incubated for four days and then scored for Arg$^+$mutant colonies. Viable counts were obtained by plating 100 $\mu$l of suitably diluted samples from four randomly chosen wells onto nutrient agar, followed by overnight incubation at 37° C.

Detection of fluorescence emission from fusion strain cultures in microtiter plates. Culture growth conditions and experimental protocols were performed generally as described above in Example 1. Between 10 and 50 cells from a suitably diluted logarithmic phase culture were used to inoculate parallel 150 $\mu$l cultures in 96 well flat bottomed microtiter plates (Elkay), and incubated at 37° C. with shaking. Fluorescence was quantified using a Fluoroskan Ascent by Labsystems, using an emission filter of 520nm and an excitation filter of 485nm.

Statistical analysis. Statistical analysis of multiple parallel cultures to detect and compare low levels of mutation were performed using the SPSS statistical analysis software package, version 7.5. The Kolmogorov-Smirnov Z Test (KS Test), which detects differences in both the locations and shapes of data distributions, was used to analyze the fluorescent values obtained from microtiter plate assays after 24 hours incubation and the mutant colony distributions obtained after 4 day plate incubations. In all cases the zero dose control distribution was compared to distributions obtained in the presence of exogenous mutagen.

Results

Detection of chemical mutagens by revertant colony assay.

Reversion of the arg-3 marker in E. coli strain GW2100/pTJgfp was analyzed in approximately 40 parallel cultures exposed to varying doses of MNNG (FIG. 7) and MMS (FIG. 8). Exposure to 3.5 $\mu$g/ml MNNG elicited a positive response as seen by a significant increase in the mean revertant colony numbers of the 40 exposed cultures compared to the 40 zero exposure controls (FIG. 7). Likewise exposure of parallel cultures to 325 $\mu$g/ml MMS gives a clearly positive result where the mean number of revertant colonies per culture sample changes, and while this change does not occur at 13 $\mu$g/ml, mutagenicity is still detectable through a change in the culture to culture variation in mutant numbers (FIG. 8).

Direct comparison of revertant colony assay and fluorescent emission from a gene fusion.

In a single experiment, 24 parallel cultures of GW2100/pTJgfp were exposed to 1.7 $\mu$l of MNNG and both mutation at the arg-3 chromosomal locus versus transcription of the plasmid-encoded umuC'-gfp fusion analyzed (FIGS. 9a and 9b). Note from the data that the mutagenic activity of the chosen dose of MNNG can be detected by a shift in the culture to culture variation and arithmetic mean of either revertant colony numbers (FIG. 9b) or fluorescent emission (FIG. 9a) compared to unexposed controls. The latter experiment represents a substantial technical simplification to measurement protocols provided through the inherent stability of the gfp gene product. Instead of requiring the significant agar medium preparation and sample processing of a plate count, the experiment was run in a single 96 well microtiter plate and read automatically.

Confirmation of the effectiveness of the gene fusion strain in detecting other mutagens.

The ability of the umuC'-gfp fusion plasmid to detect mutagenic activity of other potent agents was confirmed. In FIG. 10 a total of 84 parallel cultures were exposed to each of 0, 13 and 325 µg/ml of the alkylating agent methylmethane sulphonate (MMS). Note that at 325 µg/ml mutagenic activity of the compound is pronounced, as shown by a substantial shift in the mean fluorescent output per culture compared to the unexposed control series. Visually there is a minor shift in the distribution of fluorescent output from cultures exposed to 13 µg/ml compared to the control series, although the mean fluorescent output of this bank of cultures is similar to the unexposed cultures. This difference was analyzed statistically as detailed below.

In a similar vein a parallel series of 84 replicate cultures were exposed to each of 0,0.1 and 3.5 µg/ml MNNG (FIG. 11). Mutagenic activity was clearly evident at 3.5 µg/ml as shown by the significant shift in the distribution of fluorescent output per culture compared to the unexposed controls. At 0.1 µg/ml a minor shift in culture to culture variation of fluorescent output was evident, and was again analyzed statistically. Finally 84 parallel cultures were exposed to 0, 1 and 3 J/m$^2$ of 254 nm ultraviolet light (UVC) (FIG. 12). The mutagenic activity of UVC is clearly evident at 3 J/m$^2$, and the minor shift evident in cultures exposed to 1 J/m$^2$ was analyzed statistically. Thus the quantification of fluorescent output can be successfully used to assess mutagenicity of both physical and chemical agents.

Statistical comparison of fluorescent emission patterns from different treatments.

Table 2 shows results of use of the KS test in detecting differences in mutation rate between unexposed banks of parallel cultures versus those exposed to low level mutagens (13 µg/ml MMS, FIG. 10; 0.1 µg/ml MNNG, FIG. 11; and 1 J/m$^2$, FIG. 12). P values of less than 0.05 result in rejection of the null hypothesis that the two fluorescence distributions being compared are similar, thus indicating a significant difference in the pattern and or location of the fluorescence output from each treatment. Although there was no marked difference between the arithmetic mean of the fluorescent output of 84 replicate cultures exposed to low doses of MMS (13.22 at 13 µg/ml, FIG. 10), MNNG (10.82 at 0.1 µg/ml, FIG. 11) or UV (14.37 at IJ/m$^2$, FIG. 12) compared to similar numbers of unexposed cultures (11.99 at 0 dose treatments in FIGS. 10–12), statistical analysis using the KS test confirmed that the distributions were significantly different from the control. Similar analyses confirmed the existence of such differences in banks of cultures exposed to higher mutagen doses that are detectable by standard colony reversion assays (Table 3). Thus, fluorescent emission from a transcriptional fusion strain can also be used to detect and quantify the effects of low dose (or weak) mutagens.

TABLE 2

Summary statistics used in comparing responses to MMS, MNNG and UV exposure, as analysed by fluorescence emission

| Dose | No mutagen | UV (J.M$^2$) | | MMS (µg/ml) | | MNNG (µg/ml) | |
|---|---|---|---|---|---|---|---|
| | | 1 | 3 | 13 | 325 | 0.1 | 3.5 |
| Mean | 11.99 | 14.37 | 17.41 | 13.22 | 36.5 | 10.82 | 19.39 |
| S.D | 0.91 | 0.78 | 1.42 | 1.28 | 3.42 | 0.61 | 1.53 |
| N | 84 | 84 | 84 | 84 | 84 | 84 | 84 |
| K.S statistic[A] | | 5.4 | 6.33 | 3.09 | 6.48 | 3.94 | 6.48 |
| Asymp. Sig. (2 tailed)[B] | | <0.000 | <0.000 | <0.000 | <0.000 | <0.000 | <0.000 |

[A]test of each mutagen versus the control;
[B]P values derived from the Kolmogorov-Smirnov 2 sample test

TABLE 3

Summary statistics used in comparing responses to MMS and MNNG exposure, as analysed by revertant colony numbers

| Dose | No Mutagen | MMS (µg/ml) | | No Mutagen | MNNG (µg/ml) | |
|---|---|---|---|---|---|---|
| | | 13 | 325 | | 0.1 | 3.5 |
| Mean | 3.53 | 8.84 | 17.95 | 4.1 | 8.05 | 24.9 |
| S.D | 0 | 5.68 | 11.22 | 4.96 | 7.7 | 38 |
| N | 37 | 37 | 37 | 40 | 40 | 40 |
| K.S statistic[A] | | 2.711 | 3.889 | | 1.789 | 3.130 |
| Asymp. Sig. (2 tailed)[B] | | <0.000 | <0.000 | | <0.003 | <0.000 |

[A]test of each mutagen versus the control;
[B]P values derived from the Kolmogorov-Smirnov 2 sample test Discussion Traditionally revertant colony counts are widely used to detect mutagenicity and provide a satisfactory tool for the analysis of potent agents. This study has shown that a transcriptional fusion strain in which an inducible DNA repair gene involved in the mutagenesis process has been fused to a reporter for fluorescent emission can also be used to detect agents that are mutagenic. Validation of the strain and the method have been presented using the known mutagens MMS, MNNG and UVC. The strain is simple to use, requires less preparation or technical proficiency during experimental execution, and yields sensitive results. The stable nature of the fluorescent protein product of the Aequerorea victoria gfp gene allows the researcher to examine the cumulative history of DNA repair gene transcription in a culture in the same way that a revertant colony count provides an end-point analysis of mutational events. The difference between the two systems may be that increased transcription of DNA repair genes is observed at lower doses than those required to induce reversion in a single gene marker. The results of this study show there is a lowering in the threshold dose of potentially hazardous chemicals that can be adequately detected by the fluorescence emission method compared to using duplicate or triplicate plate counts. The improved method thus also provides a capacity to detect weaker agents than have been analyzed to date;

weaker mutagens could be less toxic and therefore escape detection in other cellular assays.

Other reporter genes whose products are less stable than the gfp used here (e.g. the lux genes encoding bacterial luciferase) are less amenable to this type of analysis (data not shown) because they respond to more general physiological changes such as temperature, pH etc. that may confound experimental results.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

I claim:

1. A method of determining a mutagen comprising:

contacting a test compound with a host cell comprising a DNA sequence encoding a fluorescent protein operably linked to a mutagen sensitive gene, the host cell being in stationary growth phase;

monitoring a host cell preparation for the fluorescent protein; and determining a mutagen when an amount of the fluorescent protein meets or exceeds a predetermined threshold value, wherein determining further comprises statistically analyzing a difference in the location of a data distribution, a difference in a shape of a data distribution, or a combination thereof.

2. The method of claim 1, wherein the fluorescent protein comprises a green fluorescent protein.

3. The method of claim 2, wherein the fluorescent protein comprises a variant green fluorescent protein.

4. The method of claim 1, wherein the fluorescent protein comprises a variant fluorescent protein.

5. The method of claim 1, wherein the mutagen sensitive gene comprises an SOS gene.

6. The method of claim 5, wherein the mutagen sensitive gene comprises an SOS-like gene.

7. The method of claim 1, wherein the mutagen sensitive gene a variant mutagen sensitive gene.

8. The method of claim 1, wherein contacting comprises depleting a nutrient.

9. The method of claim 8, wherein contacting comprises starving the host cell.

10. The method of claim 1, wherein contacting comprises incubating host cell with a range of concentrations of the test compound.

11. The method of claim 1, wherein monitoring comprises detecting fluorescence.

12. The method of claim 11, wherein detecting fluorescence comprises employing a flourescence detector reading samples in a 96-well microtiter plate.

13. The method of claim 11, wherein detecting fluorescence comprises exciting at a wavelength comprising 485 nm and detecting emission at a wavelength comprising 510 nm, or a combination thereof.

14. The method of claim 1, wherein statistically analyzing comprises conducting a Kolmogorov-Smirnov Z Test.

15. The method of claim 14, wherein a P value of less than about 0.05 determines presence of a mutagen.

16. The method of claim 1, wherein determining comprises comparing the amount of green fluorescent protein in a host cell contacted with a test compound to a host cell contacted with a control substance.

17. The method of claim 1, further comprising providing the host cell.

18. The method of claim 17, wherein providing comprises growing the host cell to reach stationary phase.

19. A method of determining an antimutagen comprising:

contacting a test compound and a mutagen with a host cell comprising a DNA sequence encoding a fluorescent protein operably linked to a mutagen sensitive gene, the host cell being in stationary growth phase;

monitoring a host cell preparation for the fluorescent protein; and determining an antimutagen when an amount of the fluorescent protein falls below a predetermined threshold value, wherein determining further comprises statistically analyzing a difference in the location of a data distribution, a difference in a shape of a data distribution, or a combination thereof.

* * * * *

SEQUENCE LISTING

<160> NUMBER OF SEQ ID NOS: 24

<210> SEQ ID NO 1
<211> LENGTH: 1817
<212> TYPE: DNA
<213> ORGANISM: Escherichia coli

<400> SEQUENCE: 1

```
aaaatcagca gcctatgcag cgacaaatat tgatagcctg aatcagtatt gatctgctgg      60
caagaacaga ctactgtata taaaaacagt ataacttcag gcagattatt atgttgttta     120
tcaagcctgc ggatctccgc gaaattgtga cttttccgct atttagcgat cttgttcagt     180
gtggctttcc ttcaccggca gcagattacg ttgaacagcg catcgatctg aatcaactgt     240
tgatccagca tcccagcgcg acttacttcg tcaaagcaag tggtgattct atgattgatg     300
gtggaattag tgacggtgat ttactgattg tcgatagcgc tattaccgcc agccatggtg     360
atattgtcat cgctgctgtt gacggcgagt ttacggtgaa aaaattgcaa ctacgcccga     420
cggtacagct tattcccatg aacagcgcgt actcgcccat taccatcagt agtgaagata     480
cgctggatgt ctttggtgtg gtgatccacg tcgttaaggc gatgcgctga tgtttgccct     540
ctgtgatgta aacgcgtttt atgccagctg tgagacggtg tttcgccctg atttatgggg     600
taaaccggtg gttgtgctat cgaataatga cggttgcgtt atcgcccgaa acgctgaggc     660
aaaggcgctt ggcgttaaaa tgggcgatcc ctggttcaaa caaaaagatc tgtttcgtcg     720
ctgtggcgtg gtttgcttta gcagcaatta tgagctttac gcagacatga gcaatcgggt     780
gatgtcgacg ctggaagagc tatcgccccg cgtcgagatt tacagtattg atgaggcatt     840
ctgcgatctg acaggtgtgc gtaattgtcg cgatctgact gattttggca gagaaattcg     900
cgcaacggtg ctacaacgta cccatcttac tgttggtgtg gggatcgccc agaccaaaac     960
gctggctaag cttgccaatc atgcggcaaa aaaatggcag cggcagacgg gtgggtggt    1020
ggatttatca aatctggaac gccagcgtaa attaatgtct gctctccccg tggatgacgt    1080
ctggggatt ggacggcgga tcagcaaaaa actggacgcg atgggatca aaaccgttct    1140
cgatttggcg gatacagata tccggtttat ccgtaaacat tttaatgtcg tgctcgaaag    1200
aacggtgcgt gaactgcgcg gcgaaccctg tttgcaactg gaagagtttg caccgacgaa    1260
gcaggaaatt atctgttccc gctcgtttgg tgaacgcatc acgattatc cgtcgatgcg    1320
gcaggccatt tgtagttacg ctgcccgggc ggcggaaaaa cttcgcagcg agcatcaata    1380
ttgtcggttt atctccacgt ttattaagac gtcaccattt gcgctcaatg aaccttata    1440
cggcaatagc gcgtcggtaa aactgctgac gcccactcag gacagcaggg atatcattaa    1500
cgctgctacg cgatctctgg atgccatctg gcaagcgggc catcgttacc aaaaagcggg    1560
```

```
cgtgatgctg ggggatttct tcagtcaggg agtcgcgcag ctcaatttat tcgatgacaa    1620
cgcaccgcgc cccgggagtg agcaattgat gacggtaatg gatacactga atgctaaaga    1680
gggcagagga acactctatt tgccgggca ggggatccag caacaatggc agatgaagcg     1740
agccatgctt tcaccacgtt atacaacgcg aagttctgat ttactgaggg tcaaataaat    1800
atagcggcag gaaaaaa                                                   1817
```

<210> SEQ ID NO 2
<211> LENGTH: 139
<212> TYPE: PRT
<213> ORGANISM: Escherichia coli

<400> SEQUENCE: 2

```
Met Leu Phe Ile Lys Pro Ala Asp Leu Arg Glu Ile Val Thr Phe Pro
1               5                   10                  15

Leu Phe Ser Asp Leu Val Gln Cys Gly Phe Pro Ser Pro Ala Ala Asp
            20                  25                  30

Tyr Val Glu Gln Arg Ile Asp Leu Asn Gln Leu Leu Ile Gln His Pro
        35                  40                  45

Ser Ala Thr Tyr Phe Val Lys Ala Ser Gly Asp Ser Met Ile Asp Gly
    50                  55                  60

Gly Ile Ser Asp Gly Asp Leu Leu Ile Val Asp Ser Ala Ile Thr Ala
65                  70                  75                  80

Ser His Gly Asp Ile Val Ile Ala Val Asp Gly Glu Phe Thr Val
                85                  90                  95

Lys Lys Leu Gln Leu Arg Pro Thr Val Gln Leu Ile Pro Met Asn Ser
            100                 105                 110

Ala Tyr Ser Pro Ile Thr Ile Ser Ser Glu Asp Thr Leu Asp Val Phe
        115                 120                 125

Gly Val Val Ile His Val Val Lys Ala Met Arg
    130                 135
```

<210> SEQ ID NO 3
<211> LENGTH: 422
<212> TYPE: PRT
<213> ORGANISM: Escherichia coli

<400> SEQUENCE: 3

```
Met Phe Ala Leu Cys Asp Val Asn Ala Phe Tyr Ala Ser Cys Glu Thr
1               5                   10                  15

Val Phe Arg Pro Asp Leu Trp Gly Lys Pro Val Val Leu Ser Asn
            20                  25                  30

Asn Asp Gly Cys Val Ile Ala Arg Asn Ala Glu Ala Lys Ala Leu Gly
        35                  40                  45

Val Lys Met Gly Asp Pro Trp Phe Lys Gln Lys Asp Leu Phe Arg Arg
    50                  55                  60

Cys Gly Val Val Cys Phe Ser Ser Asn Tyr Glu Leu Tyr Ala Asp Met
65                  70                  75                  80

Ser Asn Arg Val Met Ser Thr Leu Glu Glu Leu Ser Pro Arg Val Glu
                85                  90                  95

Ile Tyr Ser Ile Asp Glu Ala Phe Cys Asp Leu Thr Gly Val Arg Asn
            100                 105                 110

Cys Arg Asp Leu Thr Asp Phe Gly Arg Glu Ile Arg Ala Thr Val Leu
        115                 120                 125

Gln Arg Thr His Leu Thr Val Gly Val Gly Ile Ala Gln Thr Lys Thr
```

130                 135                 140
Leu Ala Lys Leu Ala Asn His Ala Ala Lys Lys Trp Gln Arg Gln Thr
145                 150                 155                 160
Gly Gly Val Val Asp Leu Ser Asn Leu Glu Arg Gln Arg Lys Leu Met
                165                 170                 175
Ser Ala Leu Pro Val Asp Asp Val Trp Gly Ile Gly Arg Arg Ile Ser
                180                 185                 190
Lys Lys Leu Asp Ala Met Gly Ile Lys Thr Val Leu Asp Leu Ala Asp
                195                 200                 205
Thr Asp Ile Arg Phe Ile Arg Lys His Phe Asn Val Val Leu Glu Arg
                210                 215                 220
Thr Val Arg Glu Leu Arg Gly Glu Pro Cys Leu Gln Leu Glu Glu Phe
225                 230                 235                 240
Ala Pro Thr Lys Gln Glu Ile Ile Cys Ser Arg Ser Phe Gly Glu Arg
                245                 250                 255
Ile Thr Asp Tyr Pro Ser Met Arg Gln Ala Ile Cys Ser Tyr Ala Ala
                260                 265                 270
Arg Ala Ala Glu Lys Leu Arg Ser Glu His Gln Tyr Cys Arg Phe Ile
                275                 280                 285
Ser Thr Phe Ile Lys Thr Ser Pro Phe Ala Leu Asn Glu Pro Tyr Tyr
                290                 295                 300
Gly Asn Ser Ala Ser Val Lys Leu Leu Thr Pro Thr Gln Asp Ser Arg
305                 310                 315                 320
Asp Ile Ile Asn Ala Ala Thr Arg Ser Leu Asp Ala Ile Trp Gln Ala
                325                 330                 335
Gly His Arg Tyr Gln Lys Ala Gly Val Met Leu Gly Asp Phe Phe Ser
                340                 345                 350
Gln Gly Val Ala Gln Leu Asn Leu Phe Asp Asp Asn Ala Pro Arg Pro
                355                 360                 365
Gly Ser Glu Gln Leu Met Thr Val Met Asp Thr Leu Asn Ala Lys Glu
                370                 375                 380
Gly Arg Gly Thr Leu Tyr Phe Ala Gly Gln Gly Ile Gln Gln Gln Trp
385                 390                 395                 400
Gln Met Lys Arg Ala Met Leu Ser Pro Arg Tyr Thr Thr Arg Ser Ser
                405                 410                 415
Asp Leu Leu Arg Val Lys
                420

<210> SEQ ID NO 4
<211> LENGTH: 5170
<212> TYPE: DNA
<213> ORGANISM: Aequorea victoria
<220> FEATURE:
<221> NAME/KEY: misc_feature
<222> LOCATION: (193)..(201)
<223> OTHER INFORMATION: fluorescent chromophore
<221> NAME/KEY: misc_feature
<222> LOCATION: (651)..(651)
<223> OTHER INFORMATION: n is a, c, t or g

<400> SEQUENCE: 4
aagcttcaaa ttaagtcagc tccttaaatg aaagataata aagtgtagtt caagaactat      60
atgaatgatg tgttttcaga taaccaaaat ggggaaaaac atgctaaagt cagcatattt     120
ttggaaaatt gatgacgtca tcatgacgtc gttttgatga caaaacttat tataagcgaa     180
ttcttatatt tttacaggat aacaaagatg agtaaaggag aagaactttt cactggagtt     240

-continued

| | |
|---|---|
| gtcccaattc ttgttgaatt agatggtgat gttaatgggc acaaattctc tgtcagtgga | 300 |
| gagggtgaag gtgatgcaac atacggaaaa cttaccctta aatttatttg cactactgga | 360 |
| aagctacctg ttccatggcc aacacttgtc actactttct cttatggtgt tcagtaagtg | 420 |
| cattttatac tcttttaata tcagtgttaa gaaaatcaag tgtcttgcta ttttttcgat | 480 |
| tattggtgca attctagtca aattattgcg ttttttttacc caaatgttaa atgtaaaact | 540 |
| gaaatttggc acacttgcgc aaatatatac agggtatttt gaaaaaatta acaggatga | 600 |
| taaaagttgc acagaaactt atctcaagat ttacccgcag aaagatgctt naaaaattga | 660 |
| tatttgacag agcaaaacct gagattcacg tcttttagtt gtttgacttg aaattttggt | 720 |
| gacaggtagg tatcatgaaa acaaacaaa acgtaaaaat atcacgtgat taaagtgtat | 780 |
| cttacagacc agaaacagtt ttattaactt ctattattct attttgcaat atacacattg | 840 |
| tatcaatttc ttgagttact cgaagtaata ccgacctatc atcagaattt caagtcaaca | 900 |
| caacattata tggggctgat tagggaatga ttttgtctct tttagatgct tttcaagata | 960 |
| cccagatcat atgaaacagc atgactttt caagagtgcc atgccgaag gttatgtaca | 1020 |
| ggaaagaact atattttaca aagatgacgg gaactacaaa tcacgtgctg aagtcaagtt | 1080 |
| tgaaggtgat accctcgtta atagaattga gttaaaaggt attgatttta agaagatgg | 1140 |
| aaacattctt ggacacaaaa tggaatacaa ctataactca cacaatgtat acatcatggc | 1200 |
| agacaaacaa aagaatggaa tcaaagttaa cttcaaaatt gtatgtatac gttaagggca | 1260 |
| taaattttg cggcataaa atcttgcgaa atttattatc gcgaataggt tacgcaaaat | 1320 |
| ctataattaa aatgtatttt tttctgctga ttttctaaat aacaactcaa cccgtcattt | 1380 |
| ttatatcgca aaaataaatt ccgaaataat ttatgctcgc aaaaatttag gcccataagt | 1440 |
| agacttttga tatctgcgtg ctctgcaatg aagtaaaaat acgatatttt cattgaaata | 1500 |
| cacgggttca aagttatttg ttaattcaat aagcgtgcgc agaaattaaa ggacgtataa | 1560 |
| agatacgaac acatcaaacc attcatgcgt aaataatgtt ctattttaa aattcaccaa | 1620 |
| agcttaaata ttcttaagaa ttattcatgt gccatgggag caacaatata gttatggaca | 1680 |
| aaaatttctg agttcacttt tatttctgcg cgcccgcatc aaagttcaaa caactgtgaa | 1740 |
| cccgagtttt ttccagcttg caatttttaat aagagacaaa aagcaaattg cagttcaaga | 1800 |
| aaatcgagat attgccagat gtaaacattt aataagagac aaaaagttca taagcgttct | 1860 |
| aaagaacagc aacaaaataa taattagaat taaacgagtt ctcaaacaaa ataaaaactg | 1920 |
| aagtcaaaga gtcagtaagg aatttagtta acgatgcttt ataatcaaag ttttaattcc | 1980 |
| agttcatgta tgcaattaac aataagatct tggagaattg aatatgtttc gaaatttat | 2040 |
| aaattcggat ttaatttcta aagttgtgta tcaaaaatag ttcaaactat tttcatgaaa | 2100 |
| agatgataaa ttacggtaat aagtatataa tataatcaat taaaattaat tttaggctca | 2160 |
| aattacagaa tccacgtttt ttttctctag acatagcaca gtgtttagat gtttgtttta | 2220 |
| tttcatccat ccttattaca gttttcctct gaactttaat actagcgtac aatttgaata | 2280 |
| ataatctgaa atgattcaac ttttcagaga cacaacattg aagatggaag cgttcaacta | 2340 |
| gcagaccatt atcaacaaaa tactccaatt ggcgatggcc ctgtccttttt accagacaac | 2400 |
| cattacctgt ccacacaatc tgccctttcc aaagatccca acgaaaagag atcacatg | 2460 |
| atccttcttg agtttgtaac agctgctggg attacacatg gcatggatga actatacaaa | 2520 |
| taaatgtcca gacttccaat tgacactaaa gtgtccgaac aattactaaa atctcagggt | 2580 |
| tcctggttaa attcaggctg agatattatt tatatattta tagattcatt aaaatttat | 2640 |

```
gaataattta ttgatgttat taatagggdt tattttctta ttaaataggc tactggagtg   2700
cattcctaat tctatattaa ttacaatttg atttgacttg ctcagaatcc cgcttcattg   2760
cttttccact tgcattatcc ttatttagta ttaatttgta ttttggtttg gctacattga   2820
gtgcaaaaaa cctaatttc ggacgaatt tcgaacgaat tttttgacg gaattttctt     2880 cattctattt actcctctag ctaaattatt ttacctttt gttaatttgg ttaaattatt   2940
ctctgagccg atgattgaga aattaatgga ttaaaagtga gtaccttaca tgttgtcaac   3000
ttgtaacgaa tggaaaaaga aattacgttt caagagtttg aaaggtaata cagttacagt   3060
taaccgcaga aaaattgcat gatgattgat aaattcgatt tttgttatcc taaaattttc   3120
caaacgtcag tggccgacga ctttatcagg gacttctaaa agtgaaaaat aatcaggtgc   3180
ggatttcgaa ggcgcaaaac tataggaaga gagcgaaatg tcattaaatt atcatattct   3240
attaactgat gacaatagat gatgaaaagt ttatgattat tcactctcct cctgtaatta   3300 tgcgacccttt ctagattcac gcctgaaagt atagctacct gggatgaagt actagtctga   3360
ggactcttca cctaaaaatt aaattcttat aagagtaaac aagaaactta gcagttacaa   3420
acgggagagc gatgagaaac aaaaacaatt acgttgccac tatgaatatc gatgttcaat   3480
caattttgtt ccttacttat aagaacgaga tcgtcttaac ttaaaatagt aaaatgttat   3540
caagataata gcaattttt accgacacag cgaagactca ctactgaaat gatcagtttt   3600
aatcaggcaa ataatccgtg gcacataata gtgaccgaaa ataattaatc ggcattaaga   3660
ctaccgaaat aataatgttt tttctactgc gtatacgcgt gagaaatttt caataagctc   3720
atcatcttca gcatagttat acttttatgt aaagtatcaa ttccgacata aaataacggc   3780
ttattatcga aataatagcg ttttctctac tccatgcgcg tcaaaagttc tctctaggct   3840
catcatcttc agcataatta taattttgt aaagtaccag ttccggtcga aaataatgac   3900
taattaccga aattatagtg ttttttctatt gccatgcgcg tgaaaaattt tgattgaatc   3960
atcatcttca gcataggcat aattctttgt aaaatatcga ttccgacata aaataatggc   4020
ctattaccga aataatcgcg ttttttcctac tgcgcatgcg cgtcaaaaat tatatttta    4080 ttcatcatct tcagcataat tatattttt tgtaaagtac cagttccggt agaaaataat   4140
gacttgttac tgaaataata gcgttttct attgcgcatg cgctataaaa attaaagtaa   4200
cgtcatcata ttcagcatgg tattgaaatt ttcaaattta attaacctat tgaacaagaa   4260
tgtacacttg catcaaaata ggtgaaattc gccaatatcg ctaaatgtga cgcgcgggag   4320
caatactacg catgtagctt caggtaaagc atgtagaaac tcggaggagt aggagtccac   4380
cgtcgaaact aaaacgggat acactacgct atggccttcg ctctcccgta aaagggact   4440 aacaatacga cctaattgaa atactaaaaa aaacaagaga aatttaaccc ctttgttaac   4500
acttttcaaa agtgggattt tttagccaac catctggtat atatggttgc tcatttatt   4560 attatctctt tctttattgt tggtacaacg tagtcaaaat acaaattagg ttaataaaaa   4620
gcaacattat aatgtataaa atctaattgt gtctaattac cgacaaattt tacaggaaca   4680
gttttcacca gaccgagtct aatttttagt tttaaaagaa attatgtttc tactgttctg   4740
acaatctgaa gacaattagt tctagtgtaa caatgctctg aattgaatat attcagcaat   4800
attttgtttg taagaattgg atgaatgtac gaaccttcag cagatttata ccaagtgtta   4860
gatttaacaa gattttgcaag ctgatgagtt tcgagaaaat tcaacatatc tggatttgag   4920
ggtggaacat taaaatctcc taagataata attctatcat aattagaata taaattatca   4980
```

-continued

```
atgatgtcat ttaagtgatc tagaaaaata ttgatagtaa cagttggatg tttgtatata    5040
gaaatagtaa gccatctatt tttcccaaat gcgagttcaa aaaccaaaat tggattcctt    5100
caaagaaaaa agacattaag aaacttgatg gaatcccttc tcgactgtaa acaagcagtc    5160
tctgggatcc                                                          5170

<210> SEQ ID NO 5
<211> LENGTH: 218
<212> TYPE: PRT
<213> ORGANISM: Aequorea victoria
<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Ser Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met
    210                 215

<210> SEQ ID NO 6
<211> LENGTH: 736
<212> TYPE: DNA
<213> ORGANISM: Aequorea victoria
<220> FEATURE:
<221> NAME/KEY: CDS
<222> LOCATION: (14)..(730)
<223> OTHER INFORMATION:

<400> SEQUENCE: 6
aagctttatt aaa atg tct aaa ggt gaa gaa tta ttc act ggt gtt gtc    49
             Met Ser Lys Gly Glu Glu Leu Phe Thr Gly Val Val
             1               5                   10 cca att ttg gtt gaa tta gat ggt gat gtt aat ggt cac aaa ttt tct    97
Pro Ile Leu Val Glu Leu Asp Gly Asp Val Asn Gly His Lys Phe Ser
        15                  20                  25 gtc tcc ggt gaa ggt gaa ggt gat gct act tac ggt aaa ttg acc tta   145
Val Ser Gly Glu Gly Glu Gly Asp Ala Thr Tyr Gly Lys Leu Thr Leu
```

```
                30                    35                       40
aaa ttt att tgt act act ggt aaa ttg cca gtt cca tgg cca acc tta         193
Lys Phe Ile Cys Thr Thr Gly Lys Leu Pro Val Pro Trp Pro Thr Leu
 45                  50                  55                  60 gtc act act ttc ggt tat ggt gtt caa tgt ttt gct aga tac cca gat         241
Val Thr Thr Phe Gly Tyr Gly Val Gln Cys Phe Ala Arg Tyr Pro Asp
                     65                  70                  75 cat atg aaa caa cat gac ttt ttc aag tct gcc atg cca gaa ggt tat         289
His Met Lys Gln His Asp Phe Phe Lys Ser Ala Met Pro Glu Gly Tyr
                 80                  85                  90 gtt caa gaa aga act att ttt ttc aaa gat gac ggt aac tac aag acc         337
Val Gln Glu Arg Thr Ile Phe Phe Lys Asp Asp Gly Asn Tyr Lys Thr
             95                 100                 105 aga gct gaa gtc aag ttt gaa ggt gat acc tta gtt aat aga atc gaa         385
Arg Ala Glu Val Lys Phe Glu Gly Asp Thr Leu Val Asn Arg Ile Glu
        110                 115                 120 tta aaa ggt att gat ttt aaa gaa gat ggt aac att tta ggt cac aaa         433
Leu Lys Gly Ile Asp Phe Lys Glu Asp Gly Asn Ile Leu Gly His Lys
125                 130                 135                 140 ttg gaa tac aac tat aac tct cac aat gtt tac atc atg gct gac aaa         481
Leu Glu Tyr Asn Tyr Asn Ser His Asn Val Tyr Ile Met Ala Asp Lys
                145                 150                 155 caa aag aat ggt atc aaa gtt aac ttc aaa att aga cac aac att gaa         529
Gln Lys Asn Gly Ile Lys Val Asn Phe Lys Ile Arg His Asn Ile Glu
            160                 165                 170 gat ggt tct gtt caa tta gct gac cat tat caa caa aat act cca att         577
Asp Gly Ser Val Gln Leu Ala Asp His Tyr Gln Gln Asn Thr Pro Ile
        175                 180                 185 ggt gat ggt cca gtc ttg tta cca gac aac cat tac tta tcc act caa         625
Gly Asp Gly Pro Val Leu Leu Pro Asp Asn His Tyr Leu Ser Thr Gln
190                 195                 200 tct gcc tta tcc aaa gat cca aac gaa aag aga gac cac atg gtc ttg         673
Ser Ala Leu Ser Lys Asp Pro Asn Glu Lys Arg Asp His Met Val Leu
205                 210                 215                 220 tta gaa ttt gtt act gct gct ggt att acc cat ggt atg gat gaa ttg         721
Leu Glu Phe Val Thr Ala Ala Gly Ile Thr His Gly Met Asp Glu Leu
                225                 230                 235 tac aaa taa ctgcag                                                      736
Tyr Lys
```

<210> SEQ ID NO 7
<211> LENGTH: 238
<212> TYPE: PRT
<213> ORGANISM: Aequorea victoria

<400> SEQUENCE: 7

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                 20                  25                  30

Gly Glu Gly Asp Ala Thr Tyr Gly Lys Leu Thr Leu Lys Phe Ile Cys
             35                  40                  45

Thr Thr Gly Lys Leu Pro Val Pro Trp Pro Thr Leu Val Thr Thr Phe
         50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                 85                  90                  95
```

```
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr His Gly Met Asp Glu Leu Tyr Lys
225                 230                 235

<210> SEQ ID NO 8
<211> LENGTH: 29
<212> TYPE: DNA
<213> ORGANISM: Artificial Sequence
<220> FEATURE:
<223> OTHER INFORMATION: primers

<400> SEQUENCE: 8
ctcaagcttg atttctagat ttaagaagg                                    29

<210> SEQ ID NO 9
<211> LENGTH: 36
<212> TYPE: DNA
<213> ORGANISM: Artificial Sequence
<220> FEATURE:
<223> OTHER INFORMATION: Primers

<400> SEQUENCE: 9
ctcgaattct cattatttgt atagttcatc catgcc                            36

<210> SEQ ID NO 10
<211> LENGTH: 2241
<212> TYPE: DNA
<213> ORGANISM: Enterobacteriaccae

<400> SEQUENCE: 10
gatcggagcg acaggccacc cccttcctg ctagcccgcc gccacgcggc cggttacagg    60
ggacactgag aaagcagaaa gccaacaaac actatatata gcgttcgttg cagctgaag   120 cagcactaca tatagtagag aacctgtaaa acttgccaac ctgaccataa cagcgatact  180
gtataaataa acagttattt ggaagatcgc tatgaaggtc gatattttg aaagctccgg   240 cgccagccgg gtacacagca tccctttta tctgcaaaga atttctgcgg ggttccccag   300
cccggcccag ggctatgaaa agcaggagtt aaacctgcat gagtattgtg ttcgtcaccc  360
ttcagcaact tacttcctgc gggtttctgg ctcgtcaatg gaagatggcc gcatccatga  420
tggtgacgta ctggttgtgg atcgctcgct gacggccagc cacggctcaa tcgtagtcgc  480
ctgcatccat aatgaattta ccgtgaagcg actactgctg aggcccagac cctgcctgat  540
gccgatgaac aaagatttc ctgtgtacta cattgacccg gataatgaga gcgttgaaat  600
```

-continued

```
ctggggagtg gttacgcatt cccttatcga gcatccggta tgtttgcgct gattgatgtc      660
aatggcatgt acgccagctg tgagcaggca tttaggccag atctggcaaa ccgagcagtg      720
gccgttttat ccaacaatga cggcaacatt gtggcccgta attacctggc gaagaaagcg      780
ggcctgaaaa tgggcgatcc gtacttcaaa gtcagaccca taatcgagcg tcataacatc      840 gctatttta gctctaatta cactctttat gcctccatgt cggcccggtt cgcggccgta       900
gttgagtccc ttgcaagcca cgtcgaacag tattcaatcg acgagctttt tgttgactgc      960
aaagggataa cggccgccat gagccttgac gctttcgggc gccaactgcg cgaggaagtc     1020
aggcgacaca caacgctggt atgcggggtc ggtattgccc gtactaagac gctggcgaag     1080
ctgtgtaacc acgctgcaaa acatggcccc gctactggcg gggtggttgc tctggacgat     1140
ggcgccagac tgaagaaatt aatgagcatc ctgccggttg cggaagtctg ggcgtcggc      1200 catcgtacag agaaagcact cgccacaatg gggatcaaaa cggtgctgga tttagccagg     1260
gcagatacgc gcctaatccg taaaacattc ggcgttgtgc ttgaaagaac ggtacgggag     1320
ttgcgcggcg aggcttgctt cagcctggaa gaaaaccctc ctgcgaagca gcagattgtt     1380
gtgtcgcgct cattcggcca acgcgtagaa accctgacgg acatgcagca ggctgtcacc     1440
ggatttgcag cgcgcgcagc tgaaaaactg cgtaatgaga ggcaatactg ccgcgtcata     1500
agcgtcttta tccgtaccag tccttattca gtgcgtgata cacagtatgc caatcaggca     1560
accgaaaaac tgacggtggc aacccaggac agccgcacga taattcaggc agcacaagcc     1620
gcgctggcgc ggatctggcg ggaagatatt gcgtatgcaa aagcagggt catgctggca      1680 gattttagcg ggaaggaggc ccagcttgat ttattcgact ctgctacgcc ttcagctggc     1740
agcgaggctt taatggctgt tcttgatggt ataaaccggc gtggaaagaa ccagcttttt     1800
tttgcaggcc agggcatcga taactccttt gccatgcgtc gtcagatgtt gtcacctgat     1860
tacacgacag actggcgctc aataccaata gccaccatca ataattaccc ggcgccgtac     1920
ccgggccggt taaccccctca accggccgta acaagtttcg gcacggtttc gcggttttcg    1980
gtaaaagccg tttcctctgt ataaaagatc atctaaatta tgtgtattgc acaatacata     2040
tatgtgaggt tagcagtgaa tttgcctaca cccgaaacct acgatgaact tcagagagcc     2100
tacgattttt tcaatgagaa gctattcagc aacgagctgc cgccatgcct gataacgttg     2160
cagcgtgaga agcgaacgta tggctattgt tcctttaagc gtttcgtcgg ccgtgagagt     2220
gggtacacgg tagacgagat c                                                2241
```

<210> SEQ ID NO 11
<211> LENGTH: 146
<212> TYPE: PRT
<213> ORGANISM: Enterobacteriaceae

<400> SEQUENCE: 11

```
Met Lys Val Asp Ile Phe Glu Ser Ser Gly Ala Ser Arg Val His Ser
1               5                   10                  15

Ile Pro Phe Tyr Leu Gln Arg Ile Ser Ala Gly Phe Pro Ser Pro Ala
                20                  25                  30

Gln Gly Tyr Glu Lys Gln Glu Leu Asn Leu His Glu Tyr Cys Val Arg
            35                  40                  45

His Pro Ser Ala Thr Tyr Phe Leu Arg Val Ser Gly Ser Ser Met Glu
        50                  55                  60

Asp Gly Arg Ile His Asp Gly Asp Val Leu Val Val Asp Arg Ser Leu
65                  70                  75                  80
```

-continued

```
Thr Ala Ser His Gly Ser Ile Val Val Ala Cys Ile His Asn Glu Phe
             85                  90                  95

Thr Val Lys Arg Leu Leu Leu Arg Pro Arg Pro Cys Leu Met Pro Met
        100                 105                 110

Asn Lys Asp Phe Pro Val Tyr Tyr Ile Asp Pro Asp Asn Glu Ser Val
        115                 120                 125

Glu Ile Trp Gly Val Val Thr His Ser Leu Ile Glu His Pro Val Cys
    130                 135                 140

Leu Arg
145
```

<210> SEQ ID NO 12
<211> LENGTH: 421
<212> TYPE: PRT
<213> ORGANISM: Enterobacteriaceae

<400> SEQUENCE: 12

```
Met Phe Ala Leu Ile Asp Val Asn Gly Met Tyr Ala Ser Cys Glu Gln
1               5                   10                  15

Ala Phe Arg Pro Asp Leu Ala Asn Arg Ala Val Ala Val Leu Ser Asn
            20                  25                  30

Asn Asp Gly Asn Ile Val Ala Arg Asn Tyr Leu Ala Lys Lys Ala Gly
        35                  40                  45

Leu Lys Met Gly Asp Pro Tyr Phe Lys Val Arg Pro Ile Ile Glu Arg
    50                  55                  60

His Asn Ile Ala Ile Phe Ser Ser Asn Tyr Thr Leu Tyr Ala Ser Met
65                  70                  75                  80

Ser Ala Arg Phe Ala Ala Val Val Glu Ser Leu Ala Ser His Val Glu
             85                  90                  95

Gln Tyr Ser Ile Asp Glu Leu Phe Val Asp Cys Lys Gly Ile Thr Ala
        100                 105                 110

Ala Met Ser Leu Asp Ala Phe Gly Arg Gln Leu Arg Glu Glu Val Arg
        115                 120                 125

Arg His Thr Thr Leu Val Cys Gly Val Gly Ile Ala Arg Thr Lys Thr
    130                 135                 140

Leu Ala Lys Leu Cys Asn His Ala Ala Lys Thr Trp Pro Ala Thr Gly
145                 150                 155                 160

Gly Val Val Ala Leu Asp Asp Gly Ala Arg Leu Lys Lys Leu Met Ser
            165                 170                 175

Ile Leu Pro Val Ala Glu Val Trp Gly Val Gly His Arg Thr Glu Lys
        180                 185                 190

Ala Leu Ala Thr Met Gly Ile Lys Thr Val Leu Asp Leu Ala Arg Ala
        195                 200                 205

Asp Thr Arg Leu Ile Arg Lys Thr Phe Gly Val Val Leu Glu Arg Thr
    210                 215                 220

Val Arg Glu Leu Arg Gly Glu Ala Cys Phe Ser Leu Glu Glu Asn Pro
225                 230                 235                 240

Pro Ala Lys Gln Gln Ile Val Val Ser Arg Ser Phe Gly Gln Arg Val
            245                 250                 255

Glu Thr Leu Thr Asp Met Gln Gln Ala Val Thr Gly Phe Ala Ala Arg
        260                 265                 270

Ala Ala Glu Lys Leu Arg Asn Glu Arg Gln Tyr Cys Arg Val Ile Ser
        275                 280                 285

Val Phe Ile Arg Thr Ser Pro Tyr Ser Val Arg Asp Thr Gln Tyr Ala
    290                 295                 300
```

-continued

```
Asn Gln Ala Thr Glu Lys Leu Thr Val Ala Thr Gln Asp Ser Arg Thr
305                 310                 315                 320

Ile Ile Gln Ala Ala Gln Ala Ala Leu Ala Arg Ile Trp Arg Glu Asp
            325                 330                 335

Ile Ala Tyr Ala Lys Ala Gly Val Met Leu Ala Asp Phe Ser Gly Lys
        340                 345                 350

Glu Ala Gln Leu Asp Leu Phe Asp Ser Ala Thr Pro Ser Ala Gly Ser
    355                 360                 365

Glu Ala Leu Met Ala Val Leu Asp Gly Ile Asn Arg Arg Gly Lys Asn
    370                 375                 380

Gln Leu Phe Phe Ala Gly Gln Gly Ile Asp Asn Ser Phe Ala Met Arg
385                 390                 395                 400

Arg Gln Met Leu Ser Pro Asp Tyr Thr Thr Asp Trp Arg Ser Ile Pro
                405                 410                 415

Ile Ala Thr Ile Lys
            420

<210> SEQ ID NO 13
<211> LENGTH: 74
<212> TYPE: PRT
<213> ORGANISM: Enterobacteriaceae

<400> SEQUENCE: 13

Met Cys Ile Ala Gln Tyr Ile Tyr Val Arg Leu Ala Val Asn Leu Pro
1               5                   10                  15

Thr Pro Glu Thr Tyr Asp Glu Leu Gln Arg Ala Tyr Asp Phe Phe Asn
            20                  25                  30

Glu Lys Leu Phe Ser Asn Glu Leu Pro Pro Cys Leu Ile Thr Leu Gln
        35                  40                  45

Arg Glu Lys Arg Thr Tyr Gly Tyr Cys Ser Phe Lys Arg Phe Val Gly
    50                  55                  60

Arg Glu Ser Gly Tyr Thr Val Asp Glu Ile
65                  70

<210> SEQ ID NO 14
<211> LENGTH: 1990
<212> TYPE: DNA
<213> ORGANISM: Escherichia coli

<400> SEQUENCE: 14
tcgagggatt cggccggact tcaccggaca ccgggggcaa atcgccggaa actgcgggac      60
tgatcggagc gacggaccac cccccttcct gctagcccgc cgccacgcgg cggttacagg     120
ggacactgag aaagcagaaa gccaacaaac actatatata gcgttcgttg gcagctgaag     180
cagcactaca tatagtagag aacctgtaaa acttgccaac ctgaccataa cagcgatact     240
gtataaataa acagttattt ggaagatcgc tatgaaggtc gatattttg aaagctccgg      300 cgccagccgg gtacacagca tccctttta tctgcaaaga atttctgcgg ggttccccag      360
cccggcccag ggctatgaaa agcaggagtt aaacctgcat gagtattgtg ttcgtcaccc     420
ttcagcaact tacttcctgc gggtttctgg ctcgtcaatg gaagatggcc gcatccatga     480
tggtgacgta ctggttgtgg atcgctcgct gacggccagc cacggctcaa tcgtagtcgc     540
ctgcatccat aatgaattta ccgtgaagcg actactgctg aggcccagac cctgcctgat     600
gccgatgaac aaagattttc ctgtgtacta cattgacccg gataatgaga gcgttgaaat     660
ctggggagtg gttacgcatt cccttatcga gcatccggta tgtttgcgct gattgatgtc     720
```

-continued

```
aatggcatgt acgccagctg tgagcaggca tttaggccag atctggcaaa ccgagcagtg    780
gccgttttat ccaacaatga cggcaacatt gtggcccgta attacctggc gaagaaagcg    840
ggcctgaaaa tgggcgatcc gtacttcaaa gtcagaccca taatcgagcg tcataacatc    900
gctatttta gctctaatta cactctttat gcctccatgt cggcccggtt cgcggccgta    960
gttgagtccc ttgcaagcca cgtcgaacag tattcaatcg acgagctttt tgttgactgc   1020
aaagggataa cggccgccat gagccttgac gctttcgggc gccaactgcg cgaggaagtc   1080
aggcgacaca caacgctggt atgcggggtc ggtattgccc gtactaagac gctggcgaag   1140
ctgtgtaacc acgctgcaaa acatggcccc gctactggcg gggtggttgc tctggacgat   1200
ggcgccagac tgaagaaatt aatgagcatc ctgccggttg cggaagtctg gggcgtcggc   1260
catcgtacag agaaagcact cgccacaatg gggatcaaaa cggtgctgga tttagccagg   1320
gcagatacgc gcctaatccg taaaacattc ggcgttgtgc ttgaaagaac ggtacgggag   1380
ttgcgcggcg aggcttgctt cagcctggaa gaaaaccctc ctgcgaagca gcagattgtt   1440
gtgtcgcgct cattcggcca acgcgtagaa accctgacgg acatgcagca ggctgtcacc   1500
ggatttgcag cgcgcgcagc tgaaaaactg cgtaatgaga ggcaatactg ccgcgtcata   1560
agcgtcttta tccgtaccag tcctattca gtgcgtgata cacagtatgc caatcaggca   1620
accgaaaaac tgacggtggc aacccaggac agccgcacga taattcaggc agcacaagcg   1680
ctggcgcgga tctggcggga agatattgcg tatgcaaaag cagggtcat gctggcagat   1740
tttagcggga aggaggccca gcttgattta ttcgactctg ctacgccttc agctggcagc   1800
gaggctttaa tggctgttct tgatggtata accggcgtg gaaagaacca gcttttttt   1860
gcaggccagg gcatcgataa ctcctttgcc atgcgtcgtc agatgttgtc acctgattac   1920
acgacagact ggcgctcaat accaatagcc accatcaaat aattaccggc gccgtacccg   1980
ggcccctcga                                                          1990
```

<210> SEQ ID NO 15
<211> LENGTH: 146
<212> TYPE: PRT
<213> ORGANISM: Escherichia coli

<400> SEQUENCE: 15

```
Met Lys Val Asp Ile Phe Glu Ser Ser Gly Ala Ser Arg Val His Ser
1               5                   10                  15

Ile Pro Phe Tyr Leu Gln Arg Ile Ser Ala Gly Phe Pro Ser Pro Ala
            20                  25                  30

Gln Gly Tyr Glu Lys Gln Glu Leu Asn Leu His Glu Tyr Cys Val Arg
        35                  40                  45

His Pro Ser Ala Thr Tyr Phe Leu Arg Val Ser Gly Ser Ser Met Glu
    50                  55                  60

Asp Gly Arg Ile His Asp Gly Asp Val Leu Val Val Asp Arg Ser Leu
65                  70                  75                  80

Thr Ala Ser His Gly Ser Ile Val Val Ala Cys Ile His Asn Glu Phe
                85                  90                  95

Thr Val Lys Arg Leu Leu Leu Arg Pro Arg Pro Cys Leu Met Pro Met
            100                 105                 110

Asn Lys Asp Phe Pro Val Tyr Tyr Ile Asp Pro Asp Asn Glu Ser Val
        115                 120                 125

Glu Ile Trp Gly Val Val Thr His Ser Leu Ile Glu His Pro Val Cys
    130                 135                 140
```

Leu Arg
145

<210> SEQ ID NO 16
<211> LENGTH: 420
<212> TYPE: PRT
<213> ORGANISM: Escherichia coli

<400> SEQUENCE: 16

Met Phe Ala Leu Ile Asp Val Asn Gly Met Tyr Ala Ser Cys Glu Gln
1               5                   10                  15

Ala Phe Arg Pro Asp Leu Ala Asn Arg Ala Val Ala Val Leu Ser Asn
            20                  25                  30

Asn Asp Gly Asn Ile Val Ala Arg Asn Tyr Leu Ala Lys Lys Ala Gly
        35                  40                  45

Leu Lys Met Gly Asp Pro Tyr Phe Lys Val Arg Pro Ile Ile Glu Arg
    50                  55                  60

His Asn Ile Ala Ile Phe Ser Ser Asn Tyr Thr Leu Tyr Ala Ser Met
65                  70                  75                  80

Ser Ala Arg Phe Ala Ala Val Val Glu Ser Leu Ala Ser His Val Glu
                85                  90                  95

Gln Tyr Ser Ile Asp Glu Leu Phe Val Asp Cys Lys Gly Ile Thr Ala
            100                 105                 110

Ala Met Ser Leu Asp Ala Phe Gly Arg Gln Leu Arg Glu Glu Val Arg
        115                 120                 125

Arg His Thr Thr Leu Val Cys Gly Val Gly Ile Ala Arg Thr Lys Thr
    130                 135                 140

Leu Ala Lys Leu Cys Asn His Ala Ala Lys Thr Trp Pro Ala Thr Gly
145                 150                 155                 160

Gly Val Val Ala Leu Asp Asp Gly Ala Arg Leu Lys Lys Leu Met Ser
                165                 170                 175

Ile Leu Pro Val Ala Glu Val Trp Gly Val Gly His Arg Thr Glu Lys
            180                 185                 190

Ala Leu Ala Thr Met Gly Ile Lys Thr Val Leu Asp Leu Ala Arg Ala
        195                 200                 205

Asp Thr Arg Leu Ile Arg Lys Thr Phe Gly Val Val Leu Glu Arg Thr
    210                 215                 220

Val Arg Glu Leu Arg Gly Glu Ala Cys Phe Ser Leu Glu Glu Asn Pro
225                 230                 235                 240

Pro Ala Lys Gln Gln Ile Val Ser Arg Ser Phe Gly Gln Arg Val
                245                 250                 255

Glu Thr Leu Thr Asp Met Gln Gln Ala Val Thr Gly Phe Ala Ala Arg
            260                 265                 270

Ala Ala Glu Lys Leu Arg Asn Glu Arg Gln Tyr Cys Arg Val Ile Ser
        275                 280                 285

Val Phe Ile Arg Thr Ser Pro Tyr Ser Val Arg Asp Thr Gln Tyr Ala
    290                 295                 300

Asn Gln Ala Thr Glu Lys Leu Thr Val Ala Thr Gln Asp Ser Arg Thr
305                 310                 315                 320

Ile Ile Gln Ala Ala Gln Ala Leu Ala Arg Ile Trp Arg Glu Asp Ile
                325                 330                 335

Ala Tyr Ala Lys Ala Gly Val Met Leu Ala Asp Phe Ser Gly Lys Glu
            340                 345                 350

Ala Gln Leu Asp Leu Phe Asp Ser Ala Thr Pro Ser Ala Gly Ser Glu

-continued

```
                     355                 360                 365
Ala Leu Met Ala Val Leu Asp Gly Ile Asn Arg Arg Gly Lys Asn Gln
            370                 375                 380

Leu Phe Phe Ala Gly Gln Gly Ile Asp Asn Ser Phe Ala Met Arg Arg
385                 390                 395                 400

Gln Met Leu Ser Pro Asp Tyr Thr Thr Asp Trp Arg Ser Ile Pro Ile
                405                 410                 415

Ala Thr Ile Lys
            420

<210> SEQ ID NO 17
<211> LENGTH: 2574
<212> TYPE: DNA
<213> ORGANISM: Salmonella typhimurium
<220> FEATURE:
<221> NAME/KEY: CDS
<222> LOCATION: (211)..(630)
<223> OTHER INFORMATION:
<221> NAME/KEY: CDS
<222> LOCATION: (633)..(1901)
<223> OTHER INFORMATION:

<400> SEQUENCE: 17
gacgctgtac agaaaatctg gcctccaggc tggcttaaat atgcgcacat gacaatacaa        60
ccggaaaatt tacaaaaccc ataatttgaa ctgagagaga aacttacaaa cgaagcgacg       120
aagatttaaa cagtcgtagc gactccggta tcttgcgcgc atgttcaaat aacactactg       180
tatataaaaa cagtattcga ggtatggatt atg gaa ttt ttc aga cct aca gag       234
                                  Met Glu Phe Phe Arg Pro Thr Glu
                                   1               5 ttg cgc gaa att att cct ctc cca ttt ttc agt tac tta gtg ccg tgt       282
Leu Arg Glu Ile Ile Pro Leu Pro Phe Phe Ser Tyr Leu Val Pro Cys
 10              15                  20 gga ttc ccc agc ccc gcg gcg gac tac att gag cag cgt atc gat ctt       330
Gly Phe Pro Ser Pro Ala Ala Asp Tyr Ile Glu Gln Arg Ile Asp Leu
 25                  30                  35                  40 aat gag ttg ctc gtt tct cat ccc agc tca aca tat ttt gtc aaa gcc       378
Asn Glu Leu Leu Val Ser His Pro Ser Ser Thr Tyr Phe Val Lys Ala
                 45                  50                  55 tcg ggg gat tca atg att gaa gca ggc atc agc gac ggt gac ctg ctg       426
Ser Gly Asp Ser Met Ile Glu Ala Gly Ile Ser Asp Gly Asp Leu Leu
             60                  65                  70 gtg gtg gat agc tca cgg aac gct gac cac ggt gac att gta att gcg       474
Val Val Asp Ser Ser Arg Asn Ala Asp His Gly Asp Ile Val Ile Ala
         75                  80                  85 gca att gaa gga gag ttc acc gta aaa cgg ttg cag ttg cgc ccg aca       522
Ala Ile Glu Gly Glu Phe Thr Val Lys Arg Leu Gln Leu Arg Pro Thr
 90                  95                 100 gtg cag tta atc ccc atg aac ggc gcc tat cga cct ata cct gtc ggc       570
Val Gln Leu Ile Pro Met Asn Gly Ala Tyr Arg Pro Ile Pro Val Gly
105                 110                 115                 120 agt gaa gac acg ctc gac ata ttc ggg gtg gtg acc ttt atc att aaa       618
Ser Glu Asp Thr Leu Asp Ile Phe Gly Val Val Thr Phe Ile Ile Lys
                125                 130                 135 gcg gtc agt tga tt atg ttc gcg ctc tgc gat gtt aat agc ttt tac       665
Ala Val Ser     Met Phe Ala Leu Cys Asp Val Asn Ser Phe Tyr
                140                 145                 150 gcc tcc tgc gaa acg gtc ttt cgt cct gat tta tgt ggc cga ccg gtg       713
Ala Ser Cys Glu Thr Val Phe Arg Pro Asp Leu Cys Gly Arg Pro Val
                155                 160                 165
```

```
gtg gtg tta tca aac aat gat ggc tgc gtt atc gcg tgt agc gcc gag      761
Val Val Leu Ser Asn Asn Asp Gly Cys Val Ile Ala Cys Ser Ala Glu
            170                 175                 180 gcg aaa cag ctc ggt atc gca cca ggt gag cca tac ttc aaa cag aaa      809
Ala Lys Gln Leu Gly Ile Ala Pro Gly Glu Pro Tyr Phe Lys Gln Lys
        185                 190                 195 gaa cgc ttc cgg cga tcc ggt gtt gtt tgc ttc agc agt aat tac gag      857
Glu Arg Phe Arg Arg Ser Gly Val Val Cys Phe Ser Ser Asn Tyr Glu
200                 205                 210 ctt tac gct gat atg tcg aac cgg gta atg acc aca ctc gag gag atg      905
Leu Tyr Ala Asp Met Ser Asn Arg Val Met Thr Thr Leu Glu Glu Met
215                 220                 225                 230 gtg ccg cgg gta gaa att tac agc att gat gag gcc ttt tgt gat ctg      953
Val Pro Arg Val Glu Ile Tyr Ser Ile Asp Glu Ala Phe Cys Asp Leu
            235                 240                 245 acg ggg gta cga aac tgc cgg gat ctg aca gat ttc ggg cgc gag ata     1001
Thr Gly Val Arg Asn Cys Arg Asp Leu Thr Asp Phe Gly Arg Glu Ile
            250                 255                 260 aga gcg acg gtc ctg aag cgc acg cac ctg act gtc ggt gta ggc att     1049
Arg Ala Thr Val Leu Lys Arg Thr His Leu Thr Val Gly Val Gly Ile
        265                 270                 275 gcc cag acg aaa acc ctt gcc aag ctg gct aac cat gct gcg aaa aag     1097
Ala Gln Thr Lys Thr Leu Ala Lys Leu Ala Asn His Ala Ala Lys Lys
280                 285                 290 tgg cag cgc cag acc gac ggg gtg gtt gac ttg tcg aac atc gat cgc     1145
Trp Gln Arg Gln Thr Asp Gly Val Val Asp Leu Ser Asn Ile Asp Arg
295                 300                 305                 310 cag cgt cgg ctg ctg gcc ctg ata ccc gtg gag gat gtc tgg ggt gtc     1193
Gln Arg Arg Leu Leu Ala Leu Ile Pro Val Glu Asp Val Trp Gly Val
            315                 320                 325 ggc agg cgc atc agt aag aag ctc aat gcc ctg ggc atc aag act gct     1241
Gly Arg Arg Ile Ser Lys Lys Leu Asn Ala Leu Gly Ile Lys Thr Ala
            330                 335                 340 ctc gat ctc tct gaa caa agt acc tgg atc atc agg aaa cac ttc aat     1289
Leu Asp Leu Ser Glu Gln Ser Thr Trp Ile Ile Arg Lys His Phe Asn
        345                 350                 355 gtc gtg ctg gag cgt acc gtg aga gag ctt cgc gga gag cca tgt ctg     1337
Val Val Leu Glu Arg Thr Val Arg Glu Leu Arg Gly Glu Pro Cys Leu
        360                 365                 370 gag ctc gaa gag ttt gcg ccg gca aag cag gaa atc gtt tgt agt cgc     1385
Glu Leu Glu Glu Phe Ala Pro Ala Lys Gln Glu Ile Val Cys Ser Arg
375                 380                 385                 390 tct ttc ggc gag cgg gtc aca gac tat gag gaa atg cgc cag gct gtt     1433
Ser Phe Gly Glu Arg Val Thr Asp Tyr Glu Glu Met Arg Gln Ala Val
            395                 400                 405 tac agc tac gct gcg cgc gcg gca gaa aaa ctc cgc ggc gag cac cag     1481
Tyr Ser Tyr Ala Ala Arg Ala Ala Glu Lys Leu Arg Gly Glu His Gln
            410                 415                 420 tac tgc cgt ttc att tca aca ttc gtc aaa aca tca ccc ttt gcc ctg     1529
Tyr Cys Arg Phe Ile Ser Thr Phe Val Lys Thr Ser Pro Phe Ala Leu
            425                 430                 435 aac gag ccc tac tac ggt aac agc gcc gcg gtg acg ctt ctc acc ccc     1577
Asn Glu Pro Tyr Tyr Gly Asn Ser Ala Ala Val Thr Leu Leu Thr Pro
        440                 445                 450 acg cag gat tca cgt gac att atc aat gcg gct gtg aaa tgc ctg gat     1625
Thr Gln Asp Ser Arg Asp Ile Ile Asn Ala Ala Val Lys Cys Leu Asp
455                 460                 465                 470 aaa ata tgg cgc gac ggc cat cgc tac cag aaa gcg ggg gtg atg ctg     1673
Lys Ile Trp Arg Asp Gly His Arg Tyr Gln Lys Ala Gly Val Met Leu
                475                 480                 485
```

```
ggt gac ttc ttc agt cag ggc gta gcg caa ctc aac ctt ttc gac gat    1721
Gly Asp Phe Phe Ser Gln Gly Val Ala Gln Leu Asn Leu Phe Asp Asp
            490                 495                 500 aac gcg ccg cgc gcc ggt agt gcg aag ttg atg gaa gta ctg gac cat    1769
Asn Ala Pro Arg Ala Gly Ser Ala Lys Leu Met Glu Val Leu Asp His
        505                 510                 515 ctt aac gca aaa gac ggg aag ggg acg ctg tac ttc gcc ggg cag ggg    1817
Leu Asn Ala Lys Asp Gly Lys Gly Thr Leu Tyr Phe Ala Gly Gln Gly
    520                 525                 530 atg tcg caa cag tgg gct atg aag cga gaa atg ctt tcg cct cgg tac    1865
Met Ser Gln Gln Trp Ala Met Lys Arg Glu Met Leu Ser Pro Arg Tyr
535                 540                 545                 550 acc aca aga tac tct gat cta ctg cgt gtt aag taa cttgtgcgat         1911
Thr Thr Arg Tyr Ser Asp Leu Leu Arg Val Lys
                555                 560 caatgcctga gatggttgcc aaatcatccc cgttctctaa ccggttttgg tcgcacaaga  1971
tcacaggaac ctctcacgat gagcttgtgc gatcaatgcc tgagatggtt gccaaatcat  2031
ccccgttctc taaccggttt tggtcgcaca agatcacagg aacctctcac gatgaggcgc  2091
atgtatcctg gtttacgaca tcagaaaatg tggcgcgttt attgcccggc aggcgttgtg  2151
agacgtcact tatttacgcc aggtttcagc cgtagcgaca ggcatgaata aaaagagtat  2211
ggcaatcagc gtgataatgc taaaaacaa ttaatatttt tttaacaaaa ctaaagcttg   2271
ctatgttcag ttaaccatgc gttaatggtt gtgcggtttg atacaaactt atctgaagta  2331
gtgattgtaa tatttctcat catttgttcc tcttgagatc tcctttaggt tttttctct   2391
ctgataattt tcttcaggcc attttccgca agggctcatt cgaaaggtaa caatattatg  2451
acgacgaaaa tcactggttt agtaaaatgg tttaaccctg aaaagggctt tggtttcatt  2511
acgcctaaag atggcagcaa agatgtgttt gtgcattttt cagccattca agtaatgaa   2571
ttc                                                                 2574
```

<210> SEQ ID NO 18
<211> LENGTH: 139
<212> TYPE: PRT
<213> ORGANISM: Salmonella typhimurium

<400> SEQUENCE: 18

```
Met Glu Phe Phe Arg Pro Thr Glu Leu Arg Glu Ile Ile Pro Leu Pro
1               5                   10                  15

Phe Phe Ser Tyr Leu Val Pro Cys Gly Phe Pro Ser Pro Ala Ala Asp
            20                  25                  30

Tyr Ile Glu Gln Arg Ile Asp Leu Asn Glu Leu Leu Val Ser His Pro
        35                  40                  45

Ser Ser Thr Tyr Phe Val Lys Ala Ser Gly Asp Ser Met Ile Glu Ala
    50                  55                  60

Gly Ile Ser Asp Gly Asp Leu Leu Val Val Asp Ser Ser Arg Asn Ala
65                  70                  75                  80

Asp His Gly Asp Ile Val Ile Ala Ile Glu Gly Glu Phe Thr Val
                85                  90                  95

Lys Arg Leu Gln Leu Arg Pro Thr Val Gln Leu Ile Pro Met Asn Gly
            100                 105                 110

Ala Tyr Arg Pro Ile Pro Val Gly Ser Glu Asp Thr Leu Asp Ile Phe
        115                 120                 125

Gly Val Val Thr Phe Ile Ile Lys Ala Val Ser
    130                 135
```

<210> SEQ ID NO 19
<211> LENGTH: 422
<212> TYPE: PRT
<213> ORGANISM: Salmonella typhimurium

<400> SEQUENCE: 19

```
Met Phe Ala Leu Cys Asp Val Asn Ser Phe Tyr Ala Ser Cys Glu Thr
1               5                   10                  15

Val Phe Arg Pro Asp Leu Cys Gly Arg Pro Val Val Leu Ser Asn
            20                  25                  30

Asn Asp Gly Cys Val Ile Ala Cys Ser Ala Glu Ala Lys Gln Leu Gly
        35                  40                  45

Ile Ala Pro Gly Glu Pro Tyr Phe Lys Gln Lys Glu Arg Phe Arg Arg
    50                  55                  60

Ser Gly Val Val Cys Phe Ser Ser Asn Tyr Glu Leu Tyr Ala Asp Met
65                  70                  75                  80

Ser Asn Arg Val Met Thr Thr Leu Glu Glu Met Val Pro Arg Val Glu
                85                  90                  95

Ile Tyr Ser Ile Asp Glu Ala Phe Cys Asp Leu Thr Gly Val Arg Asn
            100                 105                 110

Cys Arg Asp Leu Thr Asp Phe Gly Arg Glu Ile Arg Ala Thr Val Leu
        115                 120                 125

Lys Arg Thr His Leu Thr Val Gly Val Gly Ile Ala Gln Thr Lys Thr
    130                 135                 140

Leu Ala Lys Leu Ala Asn His Ala Ala Lys Lys Trp Gln Arg Gln Thr
145                 150                 155                 160

Asp Gly Val Val Asp Leu Ser Asn Ile Asp Arg Gln Arg Arg Leu Leu
                165                 170                 175

Ala Leu Ile Pro Val Glu Asp Val Trp Gly Val Gly Arg Arg Ile Ser
            180                 185                 190

Lys Lys Leu Asn Ala Leu Gly Ile Lys Thr Ala Leu Asp Leu Ser Glu
        195                 200                 205

Gln Ser Thr Trp Ile Ile Arg Lys His Phe Asn Val Val Leu Glu Arg
    210                 215                 220

Thr Val Arg Glu Leu Arg Gly Glu Pro Cys Leu Glu Leu Glu Glu Phe
225                 230                 235                 240

Ala Pro Ala Lys Gln Glu Ile Val Cys Ser Arg Ser Phe Gly Glu Arg
                245                 250                 255

Val Thr Asp Tyr Glu Glu Met Arg Gln Ala Val Tyr Ser Tyr Ala Ala
            260                 265                 270

Arg Ala Ala Glu Lys Leu Arg Gly Glu His Gln Tyr Cys Arg Phe Ile
        275                 280                 285

Ser Thr Phe Val Lys Thr Ser Pro Phe Ala Leu Asn Glu Pro Tyr Tyr
    290                 295                 300

Gly Asn Ser Ala Ala Val Thr Leu Leu Thr Pro Thr Gln Asp Ser Arg
305                 310                 315                 320

Asp Ile Ile Asn Ala Ala Val Lys Cys Leu Asp Lys Ile Trp Arg Asp
                325                 330                 335

Gly His Arg Tyr Gln Lys Ala Gly Val Met Leu Gly Asp Phe Phe Ser
            340                 345                 350

Gln Gly Val Ala Gln Leu Asn Leu Phe Asp Asp Asn Ala Pro Arg Ala
        355                 360                 365

Gly Ser Ala Lys Leu Met Glu Val Leu Asp His Leu Asn Ala Lys Asp
```

|  |  |  |  | 370 |  |  |  |  | 375 |  |  |  | 380 |  |  |
|--|--|--|--|--|--|--|--|--|--|--|--|--|--|--|--|
Gly Lys Gly Thr Leu Tyr Phe Ala Gly Gln Gly Met Ser Gln Gln Trp
385 390 395 400

Ala Met Lys Arg Glu Met Leu Ser Pro Arg Tyr Thr Thr Arg Tyr Ser
        405                  410                  415

Asp Leu Leu Arg Val Lys
        420

<210> SEQ ID NO 20
<211> LENGTH: 2138
<212> TYPE: DNA
<213> ORGANISM: Salmonella typhimurium

<400> SEQUENCE: 20

| | | | | | |
|---|---|---|---|---|---|
| gatatccaaa | ctgaccccaa | aagggtaggg | ggagaatgtc | ccttgccgat | aaaactgttc | 60 |
| ccggtttgtt | atttctctgc | ccgctgttaa | aagttgaaag | ttgataactt | tgcagtaaaa | 120 |
| tgccgttatc | atatatactg | tataaatgta | cagctaagga | gaggcattaa | tgtcactaaa | 180 |
| acctatgaaa | tcagcccctg | acaccaaaga | aactatccct | ttctttggcg | agctcgtacc | 240 |
| cgcaggtttc | cctagccctg | ctgctgggtg | ggaagaggct | gaacttaatc | ttcatacgct | 300 |
| ggtggttact | catccagcca | gcacgtactt | cttgcgcgtg | acaggtgact | ccatgcagga | 360 |
| tgctcggata | cattctggtg | acgtgctggt | ggttgatcgc | tcagaaactc | cagagcaggg | 420 |
| tagtattgtt | gttgccagca | tcgacaacga | atttacagtc | aagaaactca | tcttgcggcc | 480 |
| acgtccatgc | cttatgccga | tgaacccggc | atacccacct | atctattttg | accctgaaag | 540 |
| taacgacgtt | gaaatttggg | gtgtggtgac | ttactcatta | atgaagcaca | aaaaatgtat | 600 |
| ggcctgatcg | acattaattc | ctgctactgt | gcctgcgagc | aagcattcag | gcccgatctt | 660 |
| gctggtaaac | ccgtagtagt | tttgtcaaac | aatgatgcca | gctgcatagc | ccgtaacaag | 720 |
| caggcgaaag | cccttggtat | aaaaatgggc | gagccattct | ttaaaatcaa | agatctcata | 780 |
| gaacggaaca | atgtcgctgt | tttcagttca | aactatgccc | tttattccgc | atttagttcc | 840 |
| cggtttgcat | ctgttataga | gtcactgact | ccgcgtagct | cagtgtattc | aatcgatgaa | 900 |
| ctttggtttg | atgccacgaa | tatcactggt | ttaatgactc | ttgatgccta | tggccgcatg | 960 |
| ttgcgagaag | aggtacagcg | tcagacaacg | cttacttgtg | gtgttgggat | agcaccgaca | 1020 |
| aaaacactcg | cgaaattgtg | ttctcatgct | tcaaaaacct | atccggcaac | tggcggagtt | 1080 |
| gtcgcgcttg | atgatgttac | ccgtttagaa | aagctgatgc | ggcttgtgcc | cgttgaagac | 1140 |
| gtgtggggtg | ttggcccacg | gctgggtaaa | aggcttcggt | ttatgggagt | ggaaaccgcg | 1200 |
| tttcaactat | cctgccttga | tcctgttcgg | gtacgaaagc | agttcaatgt | tgtccttgag | 1260 |
| cgtaccgtca | gggaactccg | gggggagcct | tgcatggcgc | ttgacgaaaa | tgatgtgatg | 1320 |
| aaacagcaaa | tagtcgtttc | ccgctccttc | ggtgagcgag | tcaccaacct | tcatgaaatg | 1380 |
| cagcaagcca | taaccgatta | tgcggctcgc | gctgccgaaa | aactccggca | agaaaaaggg | 1440 |
| tatgtctctg | taattggtgt | ttttatacgc | accagcccct | acgcagtaaa | tgatgtacct | 1500 |
| tattccaatc | aggctactga | aatgctggtg | actccctcca | acgacagcag | ggatattatt | 1560 |
| aatgctgcac | aacgcgcatt | aacgatctg | gaggccagaa | gtccgttatg | ctaaagcagg | 1620 |
| tgtgatgctt | tgtgatattc | gcgagcgtga | gcctcaactt | gatttgttca | ctgaatcggc | 1680 |
| ccagtaccgc | aacagtgaaa | atctcatgca | attactggat | actctcaaca | agcagggtag | 1740 |
| acacaatttg | ttttttgccg | gacaaggtat | aaaccccgtt | ttcgcaatga | agagaaatat | 1800 |

```
gctatcccct gcatatttga ctaggctggg atgatttacc aaaggttagg ttaggataag    1860
cccactaacc atcaaaaaga cataattttt ccttggtgtt tcacttcgcc ccctcactc    1920 gtccggcagc gcaatttggt tctcaaggtt acgtgttcaa aaacagctat aagattatgg    1980
tcacgcgctg taagccatgc cagaactaaa taaattggat tttttcgtaa tgaaaatata    2040
gcgacgaacg ttgcaaaact gttttattgc tacaattccc cttgttggct aaaatacata    2100
ctgtataaac tgacaggggt atccgctatg gatttaaa                           2138
```

<210> SEQ ID NO 21
<211> LENGTH: 145
<212> TYPE: PRT
<213> ORGANISM: Salmonella typhimurium

<400> SEQUENCE: 21

```
Met Ser Leu Lys Pro Met Lys Ser Ala Pro Asp Thr Lys Glu Thr Ile
1               5                   10                  15

Pro Phe Phe Gly Glu Leu Val Pro Ala Gly Phe Pro Ser Pro Ala Ala
                20                  25                  30

Gly Trp Glu Glu Ala Glu Leu Asn Leu His Thr Leu Val Val Thr His
            35                  40                  45

Pro Ala Ser Thr Tyr Phe Leu Arg Val Thr Gly Asp Ser Met Gln Asp
        50                  55                  60

Ala Arg Ile His Ser Gly Asp Val Leu Val Val Asp Arg Ser Glu Thr
65                  70                  75                  80

Pro Glu Gln Gly Ser Ile Val Val Ala Ser Ile Asp Asn Glu Phe Thr
                85                  90                  95

Val Lys Lys Leu Ile Leu Arg Pro Arg Pro Cys Leu Met Pro Met Asn
                100                 105                 110

Pro Ala Tyr Pro Pro Ile Tyr Phe Asp Pro Glu Ser Asn Asp Val Glu
            115                 120                 125

Ile Trp Gly Val Val Thr Tyr Ser Leu Met Lys His Lys Lys Cys Met
        130                 135                 140

Ala
145
```

<210> SEQ ID NO 22
<211> LENGTH: 339
<212> TYPE: PRT
<213> ORGANISM: Salmonella typhimurium

<400> SEQUENCE: 22

```
Met Tyr Gly Leu Ile Asp Ile Asn Ser Cys Tyr Cys Ala Cys Glu Gln
1               5                   10                  15

Ala Phe Arg Pro Asp Leu Ala Gly Lys Pro Val Val Leu Ser Asn
                20                  25                  30

Asn Asp Ala Ser Cys Ile Ala Arg Asn Lys Gln Ala Lys Ala Leu Gly
            35                  40                  45

Ile Lys Met Gly Glu Pro Phe Phe Lys Ile Lys Asp Leu Ile Glu Arg
        50                  55                  60

Asn Asn Val Ala Val Phe Ser Ser Asn Tyr Ala Leu Tyr Ser Ala Phe
65                  70                  75                  80

Ser Ser Arg Phe Ala Ser Val Ile Glu Ser Leu Thr Pro Arg Ser Ser
                85                  90                  95

Val Tyr Ser Ile Asp Glu Leu Trp Phe Asp Ala Thr Asn Ile Thr Gly
            100                 105                 110
```

```
Leu Met Thr Leu Asp Ala Tyr Gly Arg Met Leu Arg Glu Glu Val Gln
        115                 120                 125

Arg Gln Thr Thr Leu Thr Cys Gly Val Gly Ile Ala Pro Thr Lys Thr
    130                 135                 140

Leu Ala Lys Leu Cys Ser His Ala Ser Lys Thr Tyr Pro Ala Thr Gly
145                 150                 155                 160

Gly Val Val Ala Leu Asp Asp Val Thr Arg Leu Glu Lys Leu Met Arg
                165                 170                 175

Leu Val Pro Val Glu Asp Val Trp Gly Val Gly Pro Arg Leu Gly Lys
            180                 185                 190

Arg Leu Arg Phe Met Gly Val Glu Thr Ala Phe Gln Leu Ser Cys Leu
        195                 200                 205

Asp Pro Val Arg Val Arg Lys Gln Phe Asn Val Val Leu Glu Arg Thr
    210                 215                 220

Val Arg Glu Leu Arg Gly Glu Pro Cys Met Ala Leu Asp Glu Asn Asp
225                 230                 235                 240

Val Met Lys Gln Gln Ile Val Val Ser Arg Ser Phe Gly Glu Arg Val
                245                 250                 255

Thr Asn Leu His Glu Met Gln Gln Ala Ile Thr Asp Tyr Ala Ala Arg
            260                 265                 270

Ala Ala Glu Lys Leu Arg Gln Glu Lys Gly Tyr Val Ser Val Ile Gly
        275                 280                 285

Val Phe Ile Arg Thr Ser Pro Tyr Ala Val Asn Asp Val Pro Tyr Ser
    290                 295                 300

Asn Gln Ala Thr Glu Met Leu Val Thr Pro Ser Asn Asp Ser Arg Asp
305                 310                 315                 320

Ile Ile Asn Ala Ala Gln Arg Ala Leu Thr Asp Leu Glu Ala Arg Ser
                325                 330                 335

Pro Leu Cys

<210> SEQ ID NO 23
<211> LENGTH: 736
<212> TYPE: DNA
<213> ORGANISM: Aequorea victoria
<220> FEATURE:
<221> NAME/KEY: CDS
<222> LOCATION: (14)..(730)
<223> OTHER INFORMATION:

<400> SEQUENCE: 23
aagctttatt aaa atg tct aaa ggt gaa gaa tta ttc act ggt gtt gtc         49
            Met Ser Lys Gly Glu Glu Leu Phe Thr Gly Val Val
             1               5                  10 cca att ttg gtt gaa tta gat ggt gat gtt aat ggt cac aaa ttt tct        97
Pro Ile Leu Val Glu Leu Asp Gly Asp Val Asn Gly His Lys Phe Ser
         15                  20                  25 gtc tcc ggt gaa ggt gaa ggt gat gct act tac ggt aaa ttg acc tta       145
Val Ser Gly Glu Gly Glu Gly Asp Ala Thr Tyr Gly Lys Leu Thr Leu
 30                  35                  40 aaa ttt att tgt act act ggt aaa ttg cca gtt cca tgg cca acc tta       193
Lys Phe Ile Cys Thr Thr Gly Lys Leu Pro Val Pro Trp Pro Thr Leu
45                  50                  55                  60 gtc act act ttc ggt tat ggt gtt caa tgt ttt gct aga tac cca gat       241
Val Thr Thr Phe Gly Tyr Gly Val Gln Cys Phe Ala Arg Tyr Pro Asp
                 65                  70                  75 cat atg aaa caa cat gac ttt ttc aag tct gcc atg cca gaa ggt tat       289
His Met Lys Gln His Asp Phe Phe Lys Ser Ala Met Pro Glu Gly Tyr
             80                  85                  90
```

```
gtt caa gaa aga act att ttt ttc aaa gat gac ggt aac tac aag acc      337
Val Gln Glu Arg Thr Ile Phe Phe Lys Asp Asp Gly Asn Tyr Lys Thr
         95                 100                 105 aga gct gaa gtc aag ttt gaa ggt gat acc tta gtt aat aga atc gaa      385
Arg Ala Glu Val Lys Phe Glu Gly Asp Thr Leu Val Asn Arg Ile Glu
110                 115                 120 tta aaa ggt att gat ttt aaa gaa gat ggt aac att tta ggt cac aaa      433
Leu Lys Gly Ile Asp Phe Lys Glu Asp Gly Asn Ile Leu Gly His Lys
125                 130                 135                 140 ttg gaa tac aac tat aac tct cac aat gtt tac atc atg gct gac aaa      481
Leu Glu Tyr Asn Tyr Asn Ser His Asn Val Tyr Ile Met Ala Asp Lys
                145                 150                 155 caa aag aat ggt atc aaa gtt aac ttc aaa att aga cac aac att gaa      529
Gln Lys Asn Gly Ile Lys Val Asn Phe Lys Ile Arg His Asn Ile Glu
            160                 165                 170 gat ggt tct gtt caa tta gct gac cat tat caa caa aat act cca att      577
Asp Gly Ser Val Gln Leu Ala Asp His Tyr Gln Gln Asn Thr Pro Ile
            175                 180                 185 ggt gat ggt cca gtc ttg tta cca gac aac cat tac tta tcc act caa      625
Gly Asp Gly Pro Val Leu Leu Pro Asp Asn His Tyr Leu Ser Thr Gln
190                 195                 200 tct gcc tta tcc aaa gat cca aac gaa aag aga gac cac atg gtc ttg      673
Ser Ala Leu Ser Lys Asp Pro Asn Glu Lys Arg Asp His Met Val Leu
205                 210                 215                 220 tta gaa ttt gtt act gct gct ggt att acc cat ggt atg gat gaa ttg      721
Leu Glu Phe Val Thr Ala Ala Gly Ile Thr His Gly Met Asp Glu Leu
                225                 230                 235 tac aaa taa ctgcag                                                   736
Tyr Lys
```

<210> SEQ ID NO 24
<211> LENGTH: 238
<212> TYPE: PRT
<213> ORGANISM: Aequorea victoria

<400> SEQUENCE: 24

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val

```
                    165                 170                 175
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235
```